United States Patent [19]

Davidow et al.

[11] Patent Number: 4,937,189

[45] Date of Patent: Jun. 26, 1990

[54] **EXPRESSION AND SECRETION OF HETEROLOGOUS PROTEINS BY *YARROWIA LIPOLYTICA* TRANSFORMANTS**

[75] Inventors: Lance S. Davidow, Providence, R.I.; John R. Dezeeuw, Stonington; Arthur E. Franke, New London, both of Conn.

[73] Assignee: Pfizer Inc., New York, N.Y.

[21] Appl. No.: 841,121

[22] Filed: Mar. 18, 1986

Related U.S. Application Data

[63] Continuation-in-part of Ser. No. 789,206, Oct. 18, 1985, abandoned.

[51] Int. Cl.$^5$ .................... C12P 21/00; C12P 19/34; C12N 5/00
[52] U.S. Cl. .............................. 435/69.1; 435/69.8; 435/172.3; 435/255; 435/256; 435/259; 435/172.1; 435/320; 435/91; 435/116; 435/69.9; 935/28; 935/37; 935/56; 935/69; 536/27
[58] Field of Search ................ 435/68, 70, 172.3, 255, 435/256, 320, 172.1, 91, 116, 171; 536/27; 935/37, 28, 56, 69

[56] References Cited

U.S. PATENT DOCUMENTS

| | | | |
|---|---|---|---|
| 4,321,365 | 3/1982 | Wu et al. | 536/27 |
| 4,394,443 | 7/1983 | Weissman et al. | 435/6 |
| 4,546,082 | 10/1985 | Kurjan et al. | 435/172.3 |
| 4,628,033 | 12/1986 | DeZeeuw | 435/255 |

FOREIGN PATENT DOCUMENTS

| | | | |
|---|---|---|---|
| 0088632 | 9/1983 | European Pat. Off. | 435/68 |
| 2091271 | 7/1982 | United Kingdom | 435/68 |

OTHER PUBLICATIONS

Davidow et al., Curr. Genet. 10, 39–48 (1985).
Gaillardin et al., Curr. Genet. 10, 49–58 (1985).
Clare et al., Curr. Genet. 10, 449–452 (1986).
Eibel et al., Mol. Gen. Genet. 191, 66–73 (1983).
Moir et al., Gene, vol. 19(1), 1982, pp. 127–138; "Molecular Cloning and Characterization of Double Stranded Complementary DNA Coding for Bovine Chymosin" IEC-3.4.23.
Ogrydziak et al., J. Gen. Microbial. 128, 1225–1234 (1982).

*Primary Examiner*—Robin L. Teskin
*Attorney, Agent, or Firm*—Peter C. Richardson; J. Trevor Lumb; Gregg C. Benson

[57] ABSTRACT

Sequencing of the XPR2 and LEU2 genes of *Yarrowia lipolytica*, recombinant *Yarrowia lipolytica* cloning vehicles comprising heterologous DNA coding for the expression of mammalian protein and other polypeptides, including plasmids suited for transformation of *Y. lipolytica* hosts and incorporating a regulon homologous to the host in its untransformed state, and secretion signals for the heterologous gene; integrative expression vectors using the XPR 2 gene promoter, alkaline protease pre-proregion and XPR2 terminator region and those having the LEU2 promoter and alkaline protease secretory signal sequences capable, in a transformed *Y. lipolytica* cell culture, of expressing and secreting a heterologous protein outside the cell; *Y. lipolytica* transformants comprising said vectors and plasmids; methods for preparing vectors to direct secretion of specified heterologous proteins coded for by genes, cDNA or synthetic DNA in *Y. lipolytica* in their mature, functional state.

104 Claims, 17 Drawing Sheets

FIG. 1

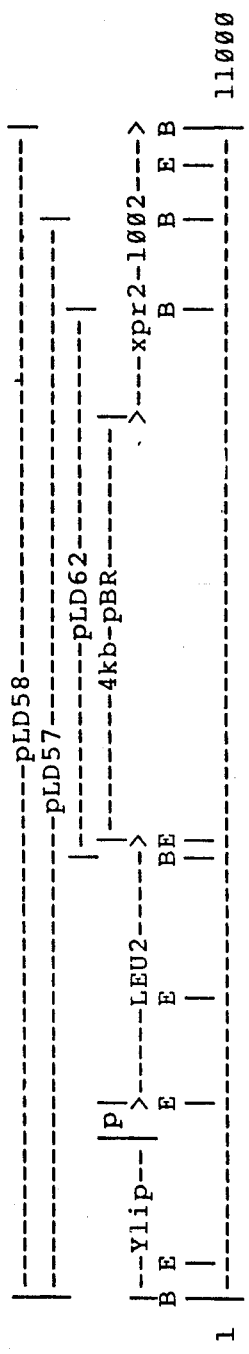

Schematic representation of the plasmids recovered from the XPR2 transformant DL112. The regions marked include (from left to right) Y. lipolytica material that was not sequenced, the small segment of pBR322 between the EcoRI site and the junction with Y. lipolytica DNA (formerly a BamHI site), the Y. lipolytica LEU2 gene, the large segment of pBR322, and the mutant allele of XPR2 which was sequenced. BglII sites are marked with "B" and EcoRI sites with "E". The three plasmids shown in linearized form were recovered as circular molecules joined at their terminal BglII sites.

FIG. 2

| I | protein sequence | val | thr | gln | trp | gly | |
|---|---|---|---|---|---|---|---|
| | mRNA 5' | GTX | ACX | CAU | TGG | GG | 3' |
| | probes 3' | CAX | TGX | GTY | ACC | CC | 5' |
| | 170   3' | CAA | TGX | GTY | ACC | CC | 5' |
| | 172   3' | CAT | TGX | GTY | ACC | CC | 5' |
| | 174   3' | CAG | TGX | GTY | ACC | CC | 5' |
| | 176   3' | CAC | TGX | GTY | ACC | CC | 5' |
| II | protein sequence | lys | lys | ala | gln | thr | |
| | mRNA 5' | AAU | AAU | GCX | CAU | AC | 3' |
| | probes 3' | TTY | TTY | CGX | GTY | TG | 5' |
| | 180   3' | TTC | TTY | CGX | GTC | TG | 5' |
| | 182   3' | TTT | TTY | CGX | GTC | TG | 5' |
| | 184   3' | TTT | TTY | CGX | GTT | TG | 5' |
| | 186   3' | TTC | TTY | CGX | GTT | TG | 5' |

FIG. 3-1

```
GATCCGGGGTTCTATGCATCCCTGAAACATTGATTGGAAATTAACATATGAGCTGCGTG

CTTTTTGCATTCAAGGGCGCAGCTTATCTTGTATCCTTAATTACACATGACCTCTTGAG

CGCCACGGTACATTCCTGGCGTCAGTTCGGTGGAGCGGACACTTTTCTCTCCTTTGTCT

GACATGTTGGTTAAGTTGTAGTCCAGGGACACAAGGGGTTCCAACGGCAGTGGCAGCCT

ACCCCACGCTACCCACCACTGGCCCTGGTCTAACTTCGACGATCGGCATCAGGGTTCAT

GGATAGGCGGTGTGATTTACGATGTGATGGACAATGTTAGAGATCCACTACTTGTA

GTCAGGCCATCTTTTACGTACGCACTGTACCATGATGTCAATGGAGTATGATGAACCGA

CTTTGAGAGACTCACATCTGCACAACACCATGTTTCAGCGGAATCCGACTTCCAACCCA

AACCCAAGCCCCTGTCAGATATCGTGAGAAGGCACGGCACCAACTAATGCACACACTCC

ACCTGTATTGCACCAAGATAATGAGGGCATCGTCTTGGCGCGTCTTGGCGAGAGCCGTG

TTTCGTGACGCAATCAGAGCAGTTTCTGGATAGTATCTTGTCCAGAAACACGATATAAA

CCCCATCGACGGGCCCGTTGAAGAGCACCAACCCACTATCCAATCCTCCAATCCAACA
```

```
-157                              -150
met lys leu ala thr ala phe thr ile leu thr ala val leu ala
ATG AAG CTC GCT ACC GCC TTT ACT ATT CTC ACT GCC GTT CTG GCC -140                                      -130
ala pro leu ala ala pro ala pro ala pro asp ala ala pro ala
GCT CCC CTG GCC GCC CCT GCC CCT GCT CCT GAT GCT GCC CCT GCT -120
ala val pro glu gly pro ala ala ala ala tyr ser ser ile leu
GCT GTG CCT GAG GGC CCT GCC GCC GCT GCC TAC TCA TCT ATT CTG -110                                         -100
ser val val ala lys gln ser lys lys phe lys his his lys arg
TCC GTG GTC GCT AAG CAG TCC AAG AAG TTT AAG CAC CAC AAG CGA -90
asp leu asp glu lys asp gln phe ile val val phe asp ser ser
GAT CTT GAT GAG AAG GAT CAG TTC ATC GTT GTC TTT GAC AGT AGC -80                                          -70
ala thr val asp gln ile ala ser glu ile gln lys leu asp ser
GCT ACT GTT GAC CAG ATC GCC TCC GAA ATC CAG AAG CTG GAC TCT -60
leu val asp glu asp ser ser asn gly ile thr ser ala leu asp
CTG GTC GAC GAG GAC TCG TCC AAC GGT ATC ACC TCT GCT CTT GAT -50                                          -40
leu pro val tyr thr asp gly ser gly phe leu gly phe val gly
CTT CCT GTC TAC ACG GAT GGA TCT GGC TTT CTC GGA TTT GTT GGA
```

FIG. 3-2

```
                                          -30
lys phe asn ser thr ile val asp lys leu lys glu ser ser val
AAG TTC AAC TCC ACT ATC GTT GAC AAG CTC AAG GAG TCG TCT GTT -20                                          -10
leu thr val glu pro asp thr ile val ser leu pro glu ile pro
CTG ACG GTC GAG CCC GAT ACC ATT GTG TCT CTC CCC GAG ATT CCT 1
ala ser ser asn ala lys arg ala ile gln thr thr pro val thr
GCT TCT TCT AAT GCC AAG CGA GCT ATC CAG ACT ACT CCC GTC ACT 10                                        20
gln trp gly leu ser arg ile ser his lys lys ala gln thr gly
CAA TGG GGC CTG TCT AGA ATC TCT CAT AAG AAG GCC CAG ACT GGA 30
asn tyr ala tyr val arg glu thr val gly lys his pro thr val
AAC TAC GCC TAC GTT CGA GAG ACA GTT GGC AAG CAC CCC ACC GTT 40                                        50
ser tyr val val asp ser gly ile arg thr thr his ser glu phe
TCT TAC GTT GTT GAC TCT GGT ATC CGA ACC ACC CAC TCC GAG TTC 60
gly gly arg ala val trp gly ala asn phe ala asp thr gln asn
GGA GGC CGA GCT GTC TGG GGA GCC AAC TTC GCT GAC ACA CAG AAC 70                                        80
ala asp leu leu gly his gly thr his val ala gly thr val gly
GCT GAT CTT CTC GGT CAC GGC ACT CAC GTT GCA GGT ACC GTG GGA 90
gly lys thr tyr gly val asp ala asn thr lys leu val ala val
GGA AAG ACA TAC GGA GTC GAC GCC AAC ACC AAG CTG GTG GCC GTC 100                                       110
lys val phe ala gly arg ser ala ala leu ser val ile asn gln
AAG GTG TTT GCA GGC CGA TCC GCA GCT CTC TCC GTC ATC AAC CAG 120
gly phe thr trp ala leu asn asp tyr ile ser lys arg asp thr
GGC TTC ACC TGG GCT CTC AAC GAC TAC ATC TCC AAG CGA GAC ACT 130                                       140
leu pro arg gly val leu asn phe ser gly gly gly pro lys ser
CTG CCT CGA GGA GTG CTG AAC TTC TCT GGA GGA GGA CCC AAG TCC 150
ala ser gln asp ala leu trp ser arg ala thr gln glu gly leu
GCT TCC CAG GAC GCC CTA TGG TCT CGA GCT ACC CAG GAG GGT CTG 160                                       170
leu val ala ile ala ala gly asn asp ala val asp ala cys asn
CTT GTC GCC ATC GCT GCG GGA AAC GAT GCC GTG GAC GCC TGT AAC
```

FIG. 3-3

```
                              180
asp ser pro gly asn ile gly gly ser thr ser gly ile ile thr
GAC TCT CCC GGT AAC ATT GGA GGC TCC ACC TCT GGT ATC ATC ACT 190                                    200
val gly ser ile asp ser ser asp lys ile ser val trp ser gly
GTG GGT TCC ATT GAC TCT AGC GAT AAG ATC TCC GTC TGG TCC GGT 210
gly gln gly ser asn tyr gly thr cys val asp val phe ala pro
GGA CAG GGA TCC AAC TAC GGA ACT TGT GTT GAT GTC TTT GCC CCC 220                                    230
gly ser asp ile ile ser ala ser tyr gln ser asp ser gly thr
GGC TCC GAT ATC ATC TCT GCC TCT TAC CAG TCC GAC TCT GGT ACT 240
leu val tyr ser gly thr ser met ala cys pro his val ala gly
TTG GTC TAC TCC GGT ACC TCC ATG GCC TGT CCC CAC GTT GCC GGT 250                                    260
leu ala ser tyr tyr leu ser ile asn asp glu val leu thr pro
CTT GCC TCC TAC TAC CTG TCC ATC AAT GAC GAG GTT CTC ACC CCT 270
ala gln val glu ala leu ile thr glu ser asn thr gly val leu
GCC CAG GTC GAG GCT CTT ATT ACT GAG TCC AAC ACC GGT GTT CTT 280                                    290
pro thr thr asn leu lys gly ser pro asn ala val ala tyr asn
CCC ACC ACC AAC CTC AAG GGC TCT CCC AAC GCT GTT GCC TAC AAC 297
gly val gly ile
GGT GTT GGC ATT TAG GCAATTAACAGATAGTTTGCCGGTGATAATTCTCTTAACCTC

CCACACTCCTTTGACATAACGATTTATGTAACGAAACTGAAATTTGACCAGATATTGTTG

TAAATAGAAAATCTGGCTTGTAGGTGGCAAAATCCCGTCTTTGTTCGTCGGTTCCCTCTG

TGACTGCTCGTCGTCCCTTTGTGTTCGACTGTCGTGTTTTGTTTTCCGTGCGTGCGCAAG

TGAGATGCCCGTGTTCGAATTCGGTAGTCGCACGGACCATCGGTTGCTCTGCACACACAC

ACACGCGAGGCTGGAACCTACATCAGAGCACTACTTGCAGGGTTGATGCAACATTCAAGA

AAAGCGCAAGCAGTGGGTGATGTATAGCAGCTAACAGCAACTACTGCTCAACATGAAAAA

GGAGGGTGTTAAGACGGCCAAGACTGCTTTCTGTCTACGCCTGAGCAACGTGCTCTGCAA

CAGAGCAACAGATAATCGCCTACGGAGACAGAGACAGAGACAGAAACAGAAACAAAAGCA

ACAGAAACTGCTGTAGTGTGTTGCAGTGAGGCGGAGATTTAACCGTATAATTCACGCTCA

GATCT
```

FIGURE 4
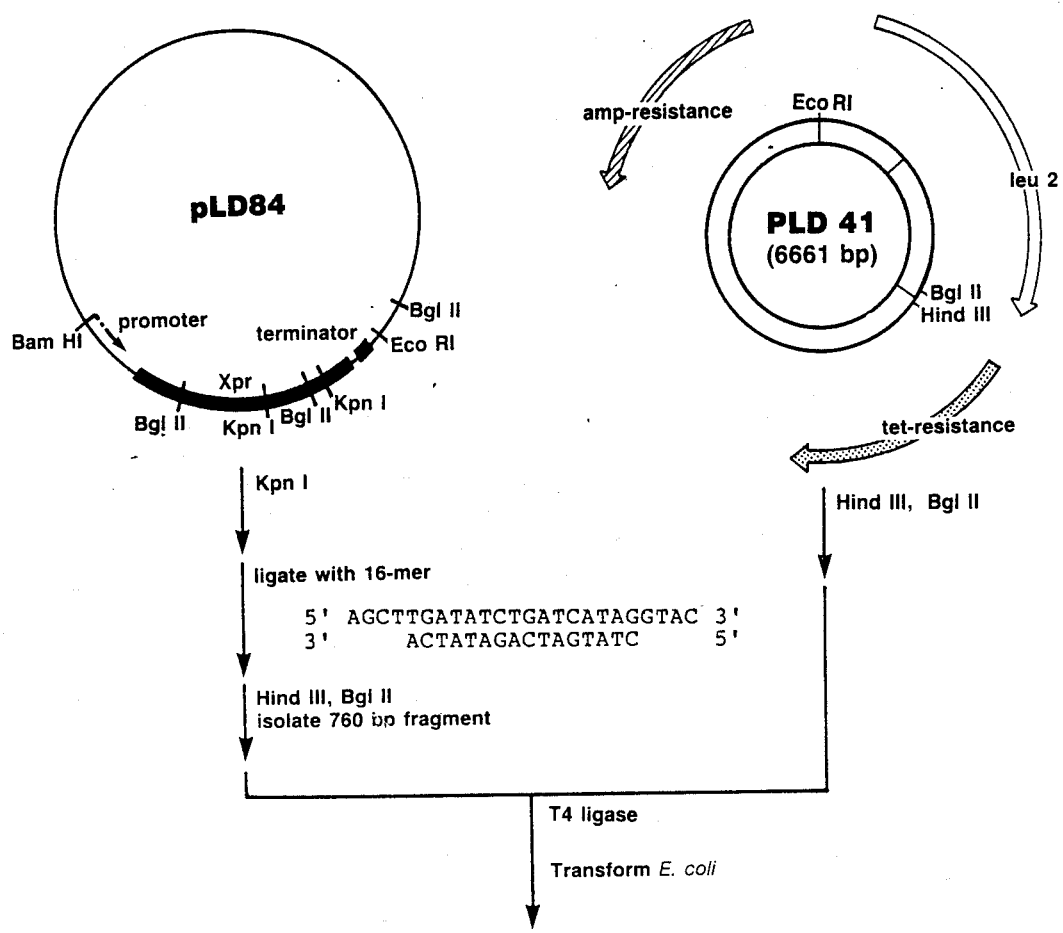
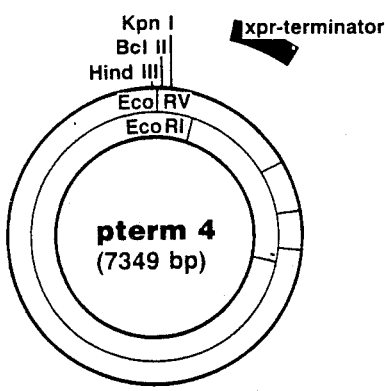

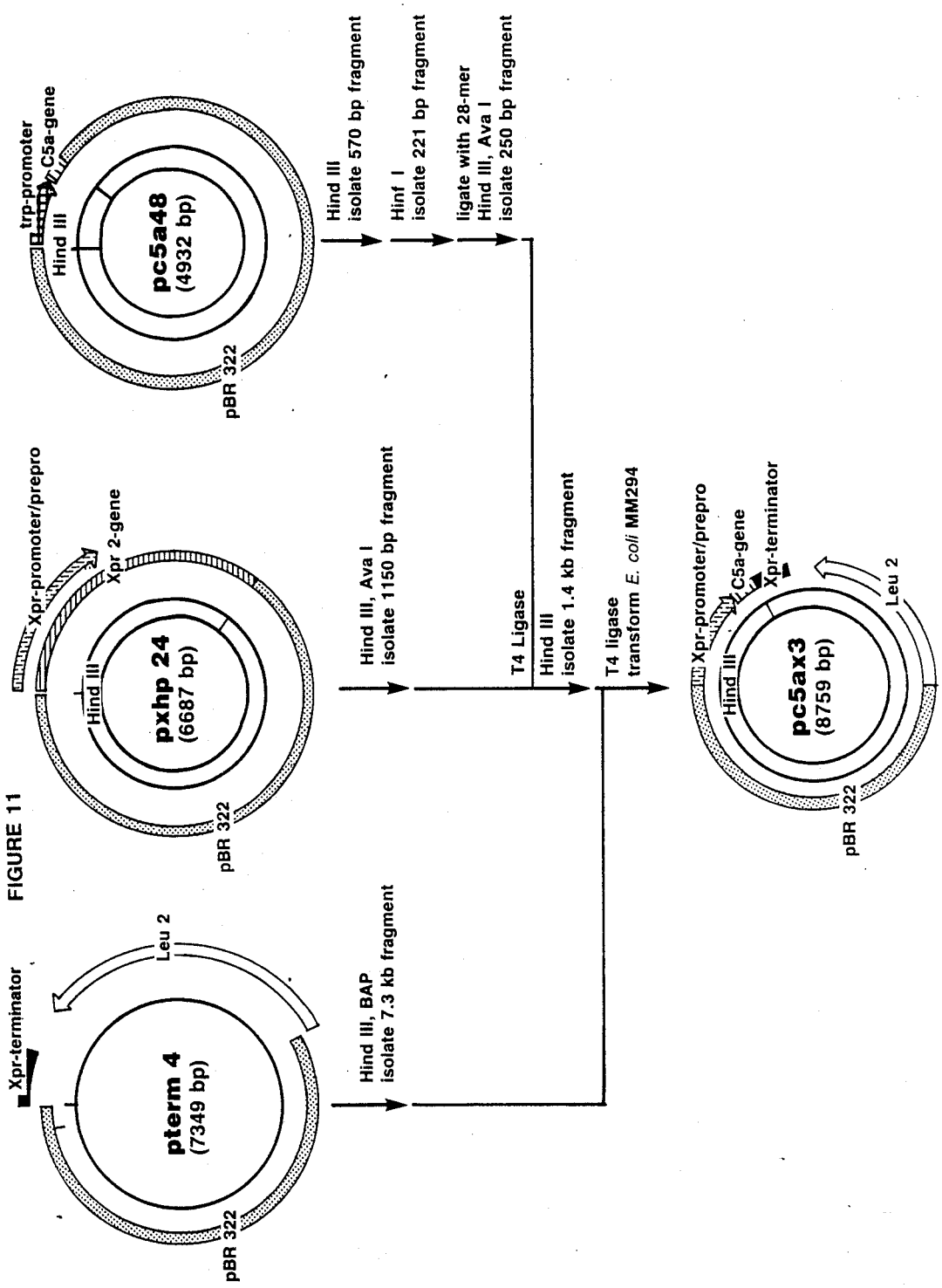

FIG.12-1

```
GTCGACACCATATCATATAAAACTAACAATGCATTGCTTATTACGAAGACTACCCGTTGCTATCTCCAC
ACCGTTATCTCCACGGTCCAAAGGCTGCTCAATGTGCTGCATACGTAACGTGGGGTGCAACCTTGAGCA
CATAGTACTTTTCCGAAAACCGGCGATAATTAAGTGTGCACTCCAACTTTTCACACTGAGCGTAAAATG
TGGAGAAGAAATCGGCACTAAAAAGTCAGGTAGACTGGAAAATGCGCCATGAAATGAATATCTCTTGCT
ACAGTAATGCCCAGCATCGAGGGGTATTGTGTCACCAACACTATAGTGGCAGCTGAAGCGCTCGTGATT
GTAGTATGAGTCTTTATTGGTGATGGGAAGAGTTCACTCAATATTCTCGTTACTGCCAAAACACCACGG
TAATCGGCCAGACACCATGGATGTAGATCACCAAGCCTGTGAATGTTATTCGAGCTAAAATGCACATGG
TTGGTGAAAGGAGTAGTTGCTGTCGAATTCCGTCGTCGCCTGAGTCATCATTTATTTACCAGTTGGCCA
CAAACCCTTGACGATCTCGTATGTCCCCTCCGACATACTCCCGGCCGGCTGGGGTACGTTCGATAGCGC
TATCGGCATCGACAAGGTTTGGGTCCCTAGCCGATACCGCACTACCTGAGTCACAATCTTCGGAGGTTT
AGTCTTCCACATAGCACGGGCAAAAGTGCGTATATATACAAGAGCGTTTGCCAGCCACAGATTTTCACT
```

```
                                              1    ------->
                                              met glu pro glu thr lys lys
CCACACACCACATCACACATACAACCACACACATCCACA       ATG GAA CCC GAA ACT AAG AAG 10                                            20
thr lys thr asp ser lys lys ile val leu leu gly gly asp phe
ACC AAG ACT GAC TCC AAG AAG ATT GTT CTT CTC GGC GGC GAC TTC 30
cys gly pro glu val ile ala glu ala val lys val leu lys ser
TGT GGC CCC GAG GTG ATT GCC GAG GCC GTC AAG GTG CTC AAG TCT 40                              .      -     50
val ala glu ala ser gly thr glu phe val phe glu asp arg leu
GTT GCT GAG GCC TCC GGC ACC GAG TTT GTG TTT GAG GAC CGA CTC 60
ile gly gly ala ala ile glu lys glu gly glu pro ile thr asp
ATT GGA GGA GCT GCC ATT GAG AAG GAG GGC GAG CCC ATC ACC GAC 70                                            80
ala thr leu asp ile cys arg lys ala asp ser ile met leu gly
GCT ACT CTC GAC ATC TGC CGA AAG GCT GAC TCT ATT ATG CTC GGT 90
ala val gly gly ala ala asn thr val trp thr thr pro asp gly
GCT GTC GGA GGC GCT GCC AAC ACC GTA TGG ACC ACT CCC GAC GGA 100                                           110
arg thr asp val arg pro glu gln gly leu leu lys leu arg lys
CGA ACC GAC GTG CGA CCC GAG CAG GGT CTC CTC AAG CTG CGA AAG 120
asp leu asn leu tyr ala asn leu arg pro cys gln leu leu ser
GAC CTG AAC CTG TAC GCC AAC CTG CGA CCC TGC CAG CTG CTG TCG
```

FIG.12-2

```
              130                                      140
pro lys leu ala asp leu ser pro ile arg asn val glu gly thr
CCC AAG CTC GCC GAT CTC TCC CCC ATC CGA AAC GTT GAG GGC ACC 150
asp phe ile ile val arg glu leu val gly gly ile tyr phe gly
GAC TTC ATC ATT GTC CGA GAG CTC GTC GGA GGT ATC TAC TTT GGA 160                                      170
glu arg lys glu asp asp gly ser gly val ala ser asp thr glu
GAG CGA AAG GAG GAT GAC GGA TCT GGC GTC GCT TCC GAC ACC GAG 180
thr tyr ser val pro glu val glu arg ile ala arg met ala ala
ACC TAC TCC GTT CCT GAG GTT GAG CGA ATT GCC CGA ATG GCC GCC 190                                      200
phe leu ala leu gln his asn pro pro leu pro val trp ser leu
TTC CTG GCC CTT CAG CAC AAC CCC CCT CTT CCC GTG TGG TCT CTT 210
asp lys ala asn val leu ala ser ser arg leu trp arg lys thr
GAC AAG GCC AAC GTG CTG GCC TCC TCT CGA CTT TGG CGA AAG ACT 220                                      230
val thr arg val leu lys asp glu phe pro gln leu glu leu asn
GTC ACT CGA GTC CTC AAG GAC GAA TTC CCC CAG CTC GAG CTC AAC 240
his gln leu ile asp ser ala ala met ile leu ile lys gln pro
CAC CAG CTG ATC GAC TCG GCC GCC ATG ATC CTC ATC AAG CAG CCC 250                                      260
ser lys met asn gly ile ile ile thr thr asn met phe gly asp
TCC AAG ATG AAT GGT ATC ATC ATC ACC ACC AAC ATG TTT GGC GAT 270
ile ile ser asp glu ala ser val ile pro gly ser leu gly leu
ATC ATC TCC GAC GAG GCC TCC GTC ATC CCC GGT TCT CTG GGT CTG 280                                      290
leu pro ser ala ser leu ala ser leu pro asp thr asn glu ala
CTG CCC TCC GCC TCT CTG GCT TCT CTG CCC GAC ACC AAC GAG GCG 300
phe gly leu tyr glu pro cys his gly ser ala pro asp leu gly
TTC GGT CTG TAC GAG CCC TGT CAC GGA TCT GCC CCC GAT CTC GGC 310                                      320
lys gln lys val asn pro ile ala thr ile leu ser ala ala met
AAG CAG AAG GTC AAC CCC ATT GCC ACC ATT CTG TCT GCC GCC ATG 330
met leu lys phe ser leu asn met lys pro ala gly asp ala val
ATG CTC AAG TTC TCT CTT AAC ATG AAG CCC GCC GGT GAC GCT GTT
```

FIG.12-3

```
         340                                          350
glu ala ala val lys glu ser val glu ala gly ile thr thr ala
GAG GCT GCC GTC AAG GAG TCC GTC GAG GCT GGT ATC ACT ACC GCC 360
asp ile gly gly ser ser ser thr ser glu val gly asp leu leu
GAT ATC GGA GGC TCT TCC TCC ACC TCC GAG GTC GGA GAC TTG TTG 370                                     380
pro thr arg ser arg ser cys ser arg arg ser lys ser phe leu
CCA ACA AGG TCA AGG AGC TGC TCA AGA AGG AGT AAG TCG TTT CTA 390
arg arg ile asp gly arg ser lys leu thr arg leu arg val gly
CGA CGC ATT GAT GGA AGG AGC AAA CTG ACG CGC CTG CGG GTT GGT 400            405
leu pro ala gly ser ala ser val OC
CTA CCG GCA GGG TCC GCT AGT GTA TAA GACTCTATAAAAGGGCCCTGCCCTGCTAATGAA

ATGATGATTTATAATTTACCGGTGTAGCAACCTTGACTAGAAGAAGCAGATTGGGTGTGTTTGTAGTGGA

GGACAGTGGTACGTTTTGGAAACAGTCTTCTTGAAAGTGTCTTGTCTACAGTATATTCACTCATAACCTC

AATAGCCAAGGGTGTAGTCGGTTTATTAAAGGAAGGGAGTTGTGGCTGATGTGGATAGATATCTTTAAGC

TGGCGACTGCACCCAACGAGTGTGGTGGTAGCTTGTTACTGTATATTCGGTAAGATATATTTTGTGGGT

TTTAGTGGTGTTTGGTAGGTTAGTGCTTGGTATATGAGTTGTAGGCATGACAATTTGGAAAGGGGTGGAC

TTTGGAATATTGTGGGATTTCAATACCTTAGTTTGTACAGGGTAATTGTTACAAATGATACAAAGAACT

GTATTTCTTTTCATTTGTTTTAATTGGTTGTATATCAAGTCCGTTAGACGAGCTCAGTGCCATGGCTTTT

GGCACTGTATTTCATTTTAGAGGTACACTACATTCAGTGAGGTATGGTAAGGTTGAGGGCATAATGAAG

GCACCTTGTACTGACAGTCACAGACCTCTCACCGAGAATTTTATGAGATATACTCGGGTTCATTTTAGGC

TCCGATTCGATTCAAATTATTACTGTCGAAATCGGTTGAGCATCCGTTGATTTCCAACAGATCTCGGCA

GTCTCTCGGATGTAGAATTAGGTTTCCTTGAGGCGAAGATCGGTTTGTGTGACATGAATT
```

EXPRESSION AND SECRETION OF HETEROLOGOUS PROTEINS BY *YARROWIA LIPOLYTICA* TRANSFORMANTS

CROSS REFERENCE TO RELATED APPLICATION

This application is a continuation-in-part of abandoned application Ser. No. 789,206, filed Oct. 18, 1985.

BACKGROUND OF THE INVENTION

1. Field of the Invention

This invention relates to yeast protein secretion technology. More specifically, it relates to recombinant *Yarrowia lipolytica* cloning vehicles comprising heterologous DNA coding for expression and secretion of mammalian protein (e.g., prochymosin) and other polypeptides; and to expression vectors comprising a *Y. lipolytica* gene promoter (e.g. XPR2 or LEU2), alkaline protease singal (or pre) sequence, pro region, and XPR2 terminator region, and variants or functional equivalents thereof arising from degeneracy of the genetic code or use of other *Y. lipolytica* gene component. Additionally, it relates to yeast transformants carrying said expression and secretion vectors, their use to produce heterologous proteins in their native, functional state; and methods for accomplishing the above.

2. Description of the Prior Art

The economic attractiveness of a steady and sufficient supply of a variety of proteins or polypeptides valuable to an industry (e.g., prorennin, bovine growth hormone) or for medicinal purposes (e.g., urogastrone, tissue plasminogen activator, human anaphylatoxin C5a) and particularly of a source which affords high quality product in an easily recoverable, functional form has led many investigators to apply recombinant DNA technology to microorganisms as "factories" for production of heterologous proteins.

Extensive research is focussed on protein secretion as a potential solution to difficulties encountered in recovering exogenous or heterologous (foreign) protein in a biologically active form from intracellular accumulations in recombinant host cells, especially from *Escherichia coli*. In *E. coli*, the heterologous protein is often produced within the cell in the form of refractile inclusion bodies. Said protein is generally of low water solubility and has little or no biological activity. Extraction of said protein from the refractile inclusion bodies generally involves harsh chemical treatment which may be costly and can result in little or no recovery of the protein in the desired, native, biologically active form. Further, the possibility of contamination of said protein with undesirable substances produced by *E. coli* is aggravated by the need to disrupt the cells in order to release the refractile bodies. Other organisms besides *E. coli* also produce heterologous protein in insoluble intracellular form. For instance, British Patent No. 2,091,271, published July 28, 1982, discloses genetic modification of *S. cerevisiae* via recombinant DNA technology to express calf rennin, or chymosin, the terms are used interchangeably herein. In view of these difficulties secretion of said protein from the host organism has been turned to in an attempt to produce the protein in a native, active configuration.

Whether a particular protein, including heterologous protein, or polypeptide is secreted by a given organism appears to be dependent upon the protein. In most eucaryotic cells, some of the protein synthesis apparatus is associated with the endoplasmic reticulum membrane and the sequence of amino acids (called the "signal sequence") near the amino-terminus of the nascent polypeptide chain serves to direct the protein to cross the membrane. The signal sequence is subsequently cleaved proteolytically during the secretion process affording active, mature protein. Several attempts have been made to develop processes for secreting heterologous proteins using signal sequences in microorganisms, including *Bacillus subtilis, Saccharomyces cerevisiae* and in mammalian cells in culture. However, said organisms have not proven to be ideal.

Inherent properties of *B. subtilis*, e.g., secretes many proteins including numerous proteases which tend to degrade the secreted heterologous protein; instability of transformed strains resulting from the loss of heterologous DNA, have hindered its development.

Mammalian cells have been successfully genetically engineered to express and secrete heterologous proteins, but these systems are technologically demanding and expensive to operate and remain impractical for commercial production of most proteins as products.

While protein secretion studies have been more successful with *S. cerevisiae* than with *B. subtilis*, even *S. cerevisiae* appears to have some inherent limitations as a protein secretion system. European Patent Application No. 0123544, published Oct. 31, 1984, describes isolation of the *S. cerevisiae* alpha-factor genes, and use of the promoter and/or signal peptide portions thereof in combination with DNA coding for proteins heterologous to yeast in a plasmid for transformation of yeast cells capable of producing discrete, mature protein upon cell culture. EP Application No. 0088632, published Sept. 14, 1983, describes a process for expressing and secreting heterologous protein in *S. cerevisiae*. However, the size of the proteins which *S. cerevisiae* will efficiently secrete with these and other secretion systems appears to be limited to about 20,000 daltons. Overcoming this general inefficiency of *S. cerevisiae* as a secretion organism has required multiple mutational alterations as described by Smith et al., Science 229; 1219-1224 (1985). One exception to this trend is the observation that Aspergillus enzymes larger than 20,000 apparently can be secreted by *S. cerevisiae*, but these enzymes are highly glycosylated by *S. cerevisiae* and this may influence the efficiency of secretion.

Particular interest resides in *Yarrowia lipolytica*, an industrially important species of yeast used to produce citric acid and single cell protein. It can also be used to produce erythritol, mannitol and isopropylmalic acid. In contrast to *S. cerevisiae*, *Y. lipolytica* is of special interest and value because of its ability to efficiently secrete high molecular weight proteins (alkaline protease, acid protease and RNAse) into its growth medium thus permitting potential recovery of heterologous proteins in the native state without the need of disrupting the producing cells. Additionally, *Y. lipolytica* secretes very few proteins in quantity thus offering potential for production of a desired heterologous protein in the growth medium as the predominant protein species and simplifying recovery of said heterologous protein product.

*Y. lipolytica* produces high levels of extracellular protease. This is the predominant protein secreted by *Y. lipolytica*. The particular protease (alkaline, acid or neutral) depends upon the strain of *Y. lipolytica* used (Ogrydziak et al., J. Gen. Microbiol. (1982) 128, 1225–1234). A partial sequence analysis of the N-terminal amino acid sequence of alkaline extracellular protease is reported by Ogrydziak et al., (loc. cit.).

Copending application Serial No. 634,505, filed July 25, 1984, describes methods for transforming *Y. lipolytica* and for cloning *Y. lipolytica* genes by complementation of mutations. It discloses the cloning of the XPR2 gene, which codes for a secreted alkaline protease, by complementation of an xpr2 mutation of *Y. lipolytica*. The methodology includes transforming a host strain of *Y. lipolytica* with a BglII partial digest of a *Y. lipolytica* gene library in the vector pLD40 described in EP application No. 0138508, published Apr. 24, 1985, the counterpart of the above-identified U.S. application.

SUMMARY OF THE INVENTION

The present invention provides methodology for preparing vectors which, when introduced into *Y. lipolytica* hosts, impart to the hosts the ability to produce and secrete specific proteins coded for by heterologous DNA from any source, but especially from eucaryotic and synthetic DNA, into the medium; recombinant *Y. lipolytica* cloning vehicles comprising heterologous DNA coding for expression of mammalian protein and other polypeptides, including plasmids suitable for transformation of *Y. lipolytica* hosts, and especially integrative expression vectors comprising the LEU2 gene promoter, the XPR2 gene promoter, alkaline protease prepro region, and XPR2 terminator region; and expression plasmids having a heterologous coding sequence with XPR2 secretion signals downstream of the LEU2 promoter which are capable of expressing and secreting a heterologous protein in *Y. lipolytica* transformed therewith.

The invention thus illustrates the expression and secretion of mature heterologous protein, and especially of prorennin and human anaphylatoxin C5a, from genetically altered cell cultures of *Y. lipolytica*. The discovery of the precise identity of the amino acid sequence as well as the DNA sequence for the exocellular alkaline protease of *Y. lipolytica* has made possible the determination that heterologous protein can be expressed and secreted via recombinant DNA techniques for production in cell culture. In the case of prorennin, the mature form of the zymogen (rennin precursor) is expressed and secreted.

It has now been found that *Y. lipolytica*, can be genetically modified via recombinant DNA technology to produce transformants capable of expressing and secreting heterologous proteins in their native form. This is accomplished by constructing vectors carrying the signal or the signal and the first (pro1) or both pro sequences (pro1+pro2) of the XPR2 gene linked to the structural gene sequence of the heterologous protein which it is desired to secrete.

Transformants produced by integration at the XPR2 locus of vector DNA comprising a fragment of the XPR2 gene missing regulatory or structural components at both ends of the gene no longer produce alkaline protease, a characteristic not only desirable for heterologous protein secretion but which can be used to screen for putative transformants.

Further, vectors carrying the XPR2 promoter and sequences for alkaline protease secretory signal sequence are capable, in a transformed *Y. lipolytica* cell, of achieving secretion of the mature heterologous protein. Some recombinant DNA vectors of this type are capable of achieving expression/secretion independent of the site of integration in a yeast genome. In general, vectors containing sufficient 5' and 3' flanking DNA afford expression of product regardless of the site of integration.

It has further been surprisingly and unexpectedly found that integration of a pBR322 derived plasmid into *Y. lipolytica* chromosomal DNA provides a region of homology which is able to foster further site-directed integrative transformation. The integrated copy of pBR322 thus serves as a "docking platform" for incoming transforming DNA. The integration of a resident copy of pBR322 into *Y. lipolytica* chromosomal DNA, despite the fact pBR322 is not native *Y. lipolytica* DNA, thus provides a known target for integration. *Y. lipolytica* transformation recipients comprising such a site afford two major advantanges over recipients lacking such a site; namely, the presence of a region having a known sequence and known restriction map to serve as a target for site-directed integration; and, the opportunity to determine, by using pBR322 as the integration target, if the input plasmid contained a complete functional unit or gene as opposed to only a portion of the desired gene. For example, a plasmid containing only a 3' fragment of the XPR2 gene could transform an XPR2-1002 recipient if it contained the wild type codon and integrated at the XPR2 locus. However, the same plasmid would not transform the XPR2-1002 host to the protease positive phenotype if it integrated into pBR322 because it lacked the entire functional unit.

Thus, in *Y. lipolytica* transformants comprising a region of homology to heterologous vector DNA, said region comprising exogenous DNA serves as a recipient site during integrative transformation of said *Y. lipolytica*. In addition to pBR322 and derivatives thereof, cosmids, bacteriophage such as M13 and lambda, synthetically derived DNA and common plasmids such as pUC13 can be used to produce *Y. lipolytica* transformants having a docking platform.

By "LEU2" promoter sequence is meant the upstream untranslated region upstream of the ATG which contains most, if not all, features required for expression.

By "XPR2" promoter sequence is meant the upstream untranslated region in front of the signal (or pre) sequence which is necessary for expression. Additionally, the signal, with or without the pro sequence, from the XPR2 gene can be used to secrete proteins under expression control of *Y. lipolytica* promoters other than that of the XPR2 gene. Thus, vectors carrying the LEU2 promoter and sequences for alkaline protease secretory signal are capable, in a transformed *Y. lipolytica* cell, of achieving secretion of mature heterologous protein.

Human anaphylatoxin C5a, also known as human complement protein C5a (human C5a), is a bioactive polypeptide fragment generated in vivo as a result of complement activation. It functions as an immunomodulator in regulating certain aspects of the humoral and cellular immune response. Its primary structure, and that of other anaphylatoxins, has been elucidated. A summary of the chemical, physical and biological characterization is presented by Hugli in "Complement", edited by H. J. Muller-Eberhard and P. A. Miescher, pages 73–99, 1985, Springer-Verlag, New York.

It will be appreciated by those skilled in the art that heterologous DNA coding for virtually any known amino acid sequence can be employed mutatis mutandi in the present invention. The methodology disclosed herein is applicable mutatis mutandi to the production and secretion of any known heterologous protein, representative members of which are enumerated in U.S. Pat. No. 4,532,207 issued July 30, 1985. Additionally, any other gene of *Y. lipolytica* secreted proteins, such as the ribonuclease and the acid protease genes, can be used in place of the XPR2 gene as can hybrid genes constructed by combining fragments of two or more of said genes, e.g., the signal sequence of the XPR2 gene and the promoter sequence of the ribonuclease gene.

Also included within the scope of this invention are the functional equivalents of the herein-described DNA or nucleotide sequences. The degeneracy of the genetic code permits substitution of certain codons by other codons which specify the same amino acid and hence would give rise to the same protein. The DNA or nucleotide sequence can vary substantially since, with the exception of methionine and tryptophan, the known amino acids can be coded for by more than one codon. Thus, portions or all of the XPR2 gene could be synthesized to give a DNA sequence significantly different from that shown in FIG. 3. The encoded amino acid sequence thereof would, however, be preserved. Such functional alterations of a given DNA or nucleotide sequence afford opportunity to promote secretion and/or processing of heterologous proteins encoded for by foreign DNA sequences fused thereto. All variations of the nucleotide sequence of the XPR2 gene and fragments thereof permitted by the genetic code are, therefore, included in this invention. Further, it is possible to delete codons or to substitute one or more codons by codons other than degenerate codons to produce a structurally modified polypeptide but one which has substantially the same utility or activity of the polypeptide produced by the unmodified DNA molecule. Said two polypeptides are functionally equivalent, as are the two DNA molecules which give rise to their production, even though the differences between said DNA molecules are not related to degeneracy of the genetic code. The simplest example of this is found in prorennin A and prorennin B, the two allelic forms of prorennin, which differ only in the presence of an aspartate residue at position 286 in prorennin A and a glycine residue at that position in prorennin B.

Utilizing this methodology, expression and excretion of the heterologous mammalian proteins prorennin and human anaphylatoxin C5a have been achieved in *Y. lipolytica* using expression and secretion signals from *Y. lipolytica* XPR2 and/or LEU2 genes. The DNA sequences for prorennin and human anaphylatoxin C5a were linked via synthetic oligonucleotides to the XPR2 gene sequence at sites presumed to code for the alkaline protease signal peptide or protease precursor processing sites, designated herein as pro1 and pro2, and used to produce gene constructs which were then inserted into *Y. lipolytica* by integrative transformation. The recombinant cultures expressed and exported into the growth medium heterologous proteins having the molecular weight and immunoreactivities of prorennin and human anaphylatoxin C5a. The prorennin thus produced is believed to be folded in a native configuration since following removal of the propeptide it exhibits full enzymatic activity.

The term "recombinant DNA material" as used herein includes any material which includes at least one of the following: the XPR2 gene of *Y. lipolytica*, the signal (or pre), the pro1, and pro2- (which together comprise the pro region) the promoter or the terminator sequence thereof; the LEU2 promoter; and functional equivalents of the aforementioned sequences possible by reason of the degeneracy of the genetic code. Representative of said recombinant DNA material are DNA fragments, plasmids or vectors or transformants containing any or all of the aforementioned sequences.

DETAILED DESCRIPTION OF THE INVENTION

Materials. Restriction endonucleases and T4 ligase were obtained from New England Biolabs, bacterial alkaline phosphatase from Bethesda Research Laboratories, T4 polynucleotide kinase from PL-Biochemicals, and [gamma-$^{32}$p]ATP from New England Nuclear. All enzymes were used under conditions recommended by the supplier.

Media.

GPP medium-(glycerol/Proteose-peptone medium) contained (per liter): 6.7 g. glycerol, 1.6 g. Difco Proteose-peptone, 1.7 g. Difco Yeast Nitrogen Base without amino acids and ammonium sulphate, 30 mg. uracil and 0.5 ml/l polypropylene glycol mol. wt 2000 (Polysciences) in 40 mM-phosphate buffer (pH 6.8). (The polypropylene glycol was omitted when used for cultures grown for use in rennin enzyme assays). Proteose-peptone was autoclaved separately in the phosphate buffer.

YEPD medium - (yeast extract/peptone/dextrose medium) contained (per liter): 5 g. yeast extract, 10 g. peptone and 20 g. dextrose.

*E. coli* was grown in LB medium at 37° C. LB medium contained (per liter): 10 g. Bactotryptone, 10 g. Bacto yeast extract, 10 g. sodium chloride; adjusted to pH 7.5 with sodium hydroxide.

DNA Sequence Analysis. The DNA fragments from the various plasmids described herein were isolated on polyacrylamide gels and sequenced by the method of Maxam et al., Methods in Enzymology, 65, 499 (1980).

Ligation Procedures. DNA fragments, including cleaved vector plasmids, were ligated by mixing the desired components (DNA fragments with ends suitably constructed to provide correct matching), with T4 DNA ligase. Approximately 10 units of ligase were added for ug quantities of vector and insert fragments. The resulting ligation reaction was transformed into competent cells of *E. coli* K12 strain MM294 (ATCC-33625) or HB101 (ATCC-33694).

Preparation of Chemically Synthesized DNA. To construct the hybrid genes for expression and secretion of prorennin eight oligonucleotides were synthesized by a modified phosphoramidite procedure (Sinha et al., Tetrahedron Letters 24, 5843 (1983) on a Genetic Design 6500 (Watertown, Mass.) automated DNA synthesizer, and were purified from 6M urea-20% polyacrylamide gels. Aliquots of complementary oligonucleotides were mixed and annealed to each other at 4° C. overnight in TE (10 mM Tris-HCl, pH 8.0; 1 mM Na-EDTA). Aliquots (about 2 ug) of the double stranded oligonucleotides were phosphorylated in a 20 ul. reaction mixture containing 70 mM Tris (pH 7.6), 10 mM MgCl$_2$, 5 mM dithiothreitol, 5 mM ATP, at 37° C. using T4 polynucleotide kinase.

Preparation of Plasmid DNA. Large scale preparation of plasmid DNA were prepared by the procedure of Holmes et al., Anal. Biochem., 114, 195–197 (1981), followed by ethidium bromide-CsCl bouyant density gradient centrifugation. Miniprep amounts of plasmid DNA were prepared by the alkaline-SDS procedure of Birnboim et al., NAR 1, 1513 (1979).

Construction of the Expression/Secretion Vectors for Prorennin. A series of different constructions were made to obtain the final expression vectors. All steps are diagrammed in the accompanying figures. Generally, DNA fragments were isolated by gel electrophoresis and ligated to other fragments, or cleaved plasmid DNA, in 20 ul. of 50 mM Tris-HCl (pH 7.5), 10 mM $MgCl_2$, 20 mM dithiothreitol, 1mM ATP, and 200 units of T4 ligase at 4° C. If partial digestion of DNA with restriction endonuclease was required, optimal cleavage times were established experimentally.

Identification of Prorennin in Culture Fluid. Yeast transformants containing the expression vectors were grown overnight in GPP medium (see above). After centrifugation to remove yeast cells, 1 ml. of 50% TCA was added to each 5 ml. aliquot of culture fluid, and maintained at 4° C. for 60 minutes. Pellets were obtained by centrifugation and washed, twice, with 2 ml. of cold acetone. Precipitated protein was dissolved in 100 ul. of SDS sample buffer and aliquots electrophoresed on 10% SDS-polyacrylamide gels (Laemmli, U.K., (1970) Nature 227, 680). Gel resolved proteins were electrophoretically transferred to nitrocellulose (Schleicher and Schuell, 0.22 um) and prorennin was identified by immuno-blot analysis of slab gels (Hawkes, R. et al., (1982) Anal. Biochem. 119, 142). The filter was overlayed with rabbit antiprorennin antibody, followed by incubation with peroxidase conjugated goat anti-rabbit IgG antibody (Cappel, Malvern, Pa). The bound antibodies were detected by staining with 4-chloro-1-naphthol and hydrogen peroxide.

Milk Clotting Activity of Prorennin in Culture Fluid. The culture fluid of various *Y. lipolytica* transformants was assayed for milk clotting activity according to a modification of the method by Ernstrom, J. Dairy Sci. 41, 1664 (1958). Briefly, the assay comprises measuring the length of time required for rennin in activated culture supernatants to clot buffered skim milk, and correlating these values to a purified rennin standard. Yeast cultures (25 ml.) were grown overnight in GPP medium. After centrifugation to remove cells, 5 ml. aliquots of the culture supernatants were freeze dried under vacuum. Each lyophilized supernatant was resuspended in 300 ul. of distilled water. A dilution series of purified calf prorennin was also prepared as a control reference standard. The prorennin in the media concentrates and controls was activated by adding about 5-10 ul. of conc. HCl to give a pH of approximately 2, and incubating for one hour at 22° C. Skim milk was prepared by adding 60 g. of dry skim milk powder (Difco) into 500 ml. of 41.5 mM sodium acetate (pH 6.3) and 13.6 mM $CaCl_2$ and stirring for 20 minutes at 4° C. The substrate was used for assays immediately after being prepared. An aliquot of 60 ul. (equivalent to 1 ml. of culture supernatant) of each enzyme preparation was added to a 1 ml. aliquot of skim milk at 37° C., and clotting time recorded.

Preparation of Synthetic Oligonucleotides for C5a Gene. The oligodeoxynucleotides used in the C5a structural gene synthesis were chemically prepared by a modified phosphoramidite procedure (Sinha et al., loc. cit.) using a controlled pore glass support on a Genetic Design 6500 (Watertown, MA) automated DNA synthesizer. The protocol utilized 3% (w/v) dichloroacetic acid in dichloromethane for detritylation, in line activation of the phosphoramidites with saturated tetrazole in acetonitrile, capping with di-ethoxyphosphine tetrazolide, and oxidation with aqueous iodine/THF (Matteucci et al., 1981, J. Amer. Chem. Soc. 105, 3183). The total time per addition cycle was 14 minutes. The ten 47-mers, segments A-J of FIG. 9, were obtained in 98.8% average yield/step (by trityl analysis), deblocked by the procedure of Matteucci et al., loc. cit., ethanol precipitated from 0.3M sodium acetate, and isolated by preparative gel electrophoresis on 10% polyacrylamide-urea denaturing gels prior to annealing.

Assembly, Cloning, and Sequencing of Human C5a Gene. FIG. 9 shows the amino acid sequence of the desired protein and the arrangement of synthetic oligonucleotides needed to make a gene coding for human C5a protein. All oligomers except A and F were phosphorylated at their 5' ends with T4 polynucleotide kinase. The assembly of the gene involved two primary annealing/ligation reactions containing; oligomers A, B, I, and J; and oligomers C, D, E, F, G, and H. The resulting 94 bp and 141 bp double stranded DNA fragments were isolated after electrophoresis on a 10% polyacrylamide gel, ligated together, and their 235 bp product isolated by gel electrophoresis. The 235 bp DNA fragment containing a structural gene coding for C5a was inserted between the EcoRI and HindIII sites of pBR322 vector DNA and transformed into competent cells of *E. coli* K-12 strain HB101. Restriction analysis of plasmid DNA isolated from 6 transformants showed that 5 of the 6 clones contained a EcoRI/HindIII fragment of the correct size. The nucleotide sequence of the C5a gene region of each of these plasmids was determined by the method of Maxam et al. Methods Enzymol. 65, 499 (1980).

Construction and Characterization of C5a Expression Plasmid for *E. coli*. Procedures for DNA fragment isolation and conditions for the ligation reactions were as published by Maniatis et al., (1982) Molecular Cloning: A Laboratory Manual, Cold Spring Harbor. The *E. coli* trp promoter-operator was originally obtained from ptrpL1 (Edman et al., (1981) Nature 291, 503). The 360 bp EcoRI fragment containing the trp promoter-operator sequence used in the C5a expression plasmid (pC5a-48) was isolated from the prorennin expression plasmid ppFZ-R2, described in EP application No. 0147178, published July 3, 1985.

Identification of C5a in *Y. lipolytica* Culture Fluid. The procedure was the same as that described above for prorennin except that goat anti-C5a and rabbit anti-goat IgG (Cappel) were used in the immunoblot. The goat anti-human C5a antibody was prepared by the method of Manderino et al., J. Immunol. Methods 53, 41-50 (I1982).

The Vectors pLD40 - described in EP application 0138508, published Apr. 24, 1985.

| The Microorganisms: | |
|---|---|
| ATCC 20774 | *Yarrowia lipolytica* PC 30869 |
| ATCC 20781 | *Yarrowia lipolytica* DL112-PC-30869 transformant with XPR2 |
| ATCC 20776 | *Yarrowia lipolytica* DL-148. Transformant of *Y. lipolytica* ATCC 20688 with SnaBI digested pLS-3 |
| ATCC 20775 | *Yarrowia lipolytica* DL-144 Transformant of *Y. lipolytica* ATCC 20688 with uncut pLS-3. |
| ATCC 20777 | transformant of *Y. lipolytica* |

| | The Microorganisms: |
|---|---|
| ATCC 20778 | PC-30869 with SnaBI cleaved pC5aX-3 transformant of *Y. lipolytica* |
| ATCC 20779 | PC-30869 with SnaBI cleaved pXX-11 transformant of *Y. lipolytica* |
| ATCC 20780 | PC-30869 with SnaBI cleaved pXX-22 transformant of *Y. lipolytica* |
| ATCC 20794 | PC-30869 with SnaBI cleaved pXX-33 transformant of *Y. lipolytica* |
| ATCC 20795 | PC-30869 with pLD56 transformant of *Y. lipolytica* ATCC 20794 with NruI cleaved pLX-34 |

They have been deposited under the terms of the Budapest Treaty in the American Type Culture Collection, Rockville, Maryland, a recognized depository affording permanence of the deposits and ready accessibility thereto by the public if a patent is granted on this application. The deposits are available during pendency of this application to one determined by the Commissioner of the United States Patent and Trademark Office to be entitled thereto under 37 CFR 1.14 and 35 USC 122, and in accordance with foreign patent laws, in countries wherein counterparts of this application, or its progeny, are filed. All restrictions on the availability to the public of the microorganisms deposited will be irrevocably removed upon granting of the patent.

The taxonomic study of *Y. lipolytica* ATCC 20774 (identified in the culture collection of Pfizer Inc. as PC 30869) was conducted by Dr. J. R. DeZeeuw who provided the description which follows. The methods used are those recommended by J. L. Lodder in "The Yeasts", second edition, N. Holland Publishing Co., Amsterdam, 1970.

CBS 599, the type culture for the species *Candida lipolytica* ("The Yeasts", Second Edition, N. Holland Publishing Co., Amsterdam, 1970) and CBS 6124, the type culture for *Saccharomcopsis lipolytica* in "The Yeasts", Third Edition, were run for comparison. Earlier the species was also referred to as *Endomycopsis lipolytica*. Its imperfect state is *Candida lipolytica*. The taxonomic position of the species was settled by van der Walt and von Arx, Antonie van Leeuwenhoek, 46, 517–521 (1980). The preferred name now is *Yarrowia lipolytica*.

The cultural, morphological, and physiological characteristics of strain PC-30869 agree with the standard description for the species listed as *Saccharomycopsis lipolytica* in "The Yeasts", Third Edition, edited by Kreger-van Rij. pp. 406–408, Elsevier Science Publishers B.V., Amsterdam, 1984.

TABLE 1

Yarrowia lipolytica Strains Compared

| Pfizer Accession Number | Source | Genotype |
|---|---|---|
| PC-30265 | NRRL YB-423 (also CBS 6124), type culture in The Yeasts, 3rd edition | Wild-type diploid |
| PC-30286 | CBS 599, type culture in The Yeasts, 2nd edition | MATA wild-type haploid |
| PC-30869 | See below | MATB bio-6 leu2-40 xpr2-1002 |

PC-30869 was constructed by genetically recombining suitable mutants of *Y. lipolytica* PC-22208, a Pfizer soil isolate, and *Y. lipolytica* PC-30026, a sub-culture of NRRL Y-1094. PC-30869 differs phenotypically from its wild-type parents in (1) not producing an active exocellular alkaline protease, (2) requiring biotin for growth, and (3) requiring a source of L-leucine.

During log phase growth of PC-30869 in yeast extract-peptone-glucose (YEPD) broth, budding cells are ovoid and have an average size of 2.6×5.5 microns. On YEPD agar, pseudo- and true-mycelium are prominent. Blastospores are present, mostly as singles in pleural positions. No carotenoid pigments are evident. The culture behaves as a "B" mating haploid in crosses with authentic tester strains for the species (Table 5). Typical ascosporulation is observed on V8 agar. Carbon assimilation pattern is shown in attached Table 2. Fermentation is absent. Ammonium ion and urea, but not nitrate, are utilized as sole nitrogen sources (Table 3). Strain PC-30869 requires the vitamins thiamine and D-biotin (Table 4). Only thiamine is required by the culture's wild-type parents. No growth is observed at 37° C.

TABLE 2

| | Carbon Assimilation[a] | | | |
|---|---|---|---|---|
| Source | Reference[b] Description Listing | Culture 30265 | 30286 | 30869 |
| 1. L-Arabinose | − | − | − | − |
| 2. Cellobiose | − | − | − | − |
| 3. Erythritol | + | +++ | +++ | +++ |
| 4. D-Galactose | − | − | − | − |
| 5. D-Glucose | + | +++ | +++ | +++ |
| 6. Inositol | − | − | − | − |
| 7. Lactose | − | − | − | − |
| 8. Maltose | ± | − | − | − |
| 9. D-Mannitol | + | +++ | +++ | +++ |
| 10. Raffinose | − | − | − | − |
| 11. Ribitol | − | − | − | − |
| 12. D-Ribose | −(+) | − | − | ++ |
| 13. L-Rhamnose | − | − | − | − |
| 14. Soluble Starch | − | − | − | − |
| 15. Sucrose | − | − | − | − |
| 16. Trehalose | − | − | − | − |
| 17. D-Xylose | − | − | − | − |
| 18. Succinic Acid | + | +++ | +++ | +++ |
| 19. Citric Acid | + | +++ | +++ | +++ |

[a] Basal medium was Bacto-yeast nitrogen base supplemented with an additonal 10 mcg/l. D-biotin and with 149 mg/l. L-leucine ethyl ester. HCl to supply 100 mg/l. L-leucine.
[b] Kreger-van Rij. (loc cit.).

TABLE 3

| | Nitrogen Assimilation[a] | | | |
|---|---|---|---|---|
| Source | Reference[b] Description Listing | Culture 30265 | 30286 | 30869 |
| 1. (NH4)2SO4 | + | +++ | +++ | +++ |
| 2. KNO3 | − | − | − | − |
| 3. Urea | + | +++ | +++ | +++ |

[a] Basal medium was Bacto-yeast carbon base supplemented with 116 mg/l sodium keto-isocaproate to provide the equivalent of 100 mg/l L-leucine and with an additional 10 mcg/l D-biotin.
[b] Kreger-van Rij. (loc. cit.).

TABLE 4

| | Vitamin Requirements[a] | | | |
|---|---|---|---|---|
| Supplement to Basal[c] | Reference[b] Conclusion | Culture 30265 | 30286 | 30869 |
| 1. None | − | tr | tr | − |
| 2. Thiamine.HCl | + | +++ | +++ | − |
| 3. D-Biotin | − | tr | tr | tr |
| 4. Thamine | + | +++ | +++ | +++ |

TABLE 4-continued

| Supplement to Basal[c] | Vitamin Requirements[a] Reference[b] Conclusion | Culture 30265 | 30286 | 30869 |
|---|---|---|---|---|
| plus Biotin | | | | |

[a]Basal medium was Bacto-vitamin-free yeast base plus 149 mg/l L-leucine ethyl ester.HCl to supply 100 mg/l L-leucine.
[b]Kreger-van Rij. (loc. cit.).
[c]200 mcg/l thiamine.HCl and/or 10 mcg/l D-biotin as indicated.

TABLE 5

| | Ascosporulation | | |
|---|---|---|---|
| | | Mated Culture | |
| Tester Strain | 30265 | 30286 | 30869 |
| None (mated culture selfed) | ++ | − | − |
| 30264 (an A mating type) | ++ | − | +++ |
| 30267 (a B mating type) | ++ | +++ | − |

[a]Cultures 30264 and 30267 are haploid strains of opposite mating type kindly provided by Dr. L. J. Wickerham. They are formally described in Science 167, 1141 (1970)
[b]30264 is Wickerham's C. lipolytica YB-421
[c]30267 is Wickerham's C. lipolytica YB-423-12

TABLE 6

| | Other Characteristics | | | |
|---|---|---|---|---|
| | Reference[a] | Culture | | |
| | Value | 30265 | 30286 | 30869 |
| Cell Shape | Ovoid | Ovoid | Ovoid | Ovoid |
| Average Cell Size (microns) | (2–4.5) × (4–22) | 3.3 × 9.1 | 3.0 × 8.2 | 2.6 × 5.5 |
| Vegetative Reproduction | Budding | Budding | Budding | Budding |
| Fermentation | Absent | Absent | Absent | Absent |
| Growth at 37° C. | No | No | No | No |
| Colony Growth | The three cultures grew similarly and agreed with the literature description. Pseudo- and true-mycelium prominent. Blastospores present, mostly as singles in pleural positions. No carotenoid pigment in evidence. | | | |

[a]Kreger-van Rij. (loc. cit.).

PC-30869 differs from other strains of *Y. lipolytica* described in the patent literature as is evident from a comparison of their phenotypes (Tablews 7 and 8).

ATCC 20228 (Nubel et al., U.S. Pat. No. 4,155,811) features wild-type nutrition behaving like the type strains for the species, CBS 599 and CBS 6124. Specifically it does not require uracil, leucine, or biotin for growth and it liquefies gelatin.

ATCC 206287 (DeZeeuw et al., U.S. Pat. No. 4,407,953) unlike ATCC 20228 requires supplemental leucine for growth. Like ATCC 20228 it does not require uracil or biotin. It will also liquefy gelatin.

ATCC 20688 (EP Application No. 0138508) grows only if the medium is supplemented with both uracil and leucine. This requirement for uracil distinguishes ATCC 20688 from both ATCC 20228 and ATCC 20628. ATCC 20688 does not require biotin and it liquefies gelatin.

Culture PC-30869 differs from all of the above. It requires biotin and leucine but not uracil for growth. It does not liquefy gelatin.

TABLE 7

| | Nutritional Requirements | | | |
|---|---|---|---|---|
| | Nutrient Omitted from Listed Medium | | | |
| Culture | None | Leucine | Uracil | Biotin |
| CBS 599 | +++ | +++ | +++ | +++ |
| CBS 6124 | +++ | +++ | +++ | +++ |
| ATCC 20228 | +++ | +++ | +++ | +++ |
| ATCC 20628 | +++ | − | +++ | +++ |
| ATCC 20688 | +++ | − | − | +++ |
| PC-30869 | +++ | − | +++ | − |

The total medium contained 16.7 g/l. Bacto-Vitamin-free Yeast Base plus 100 mg/l. uracil, 100 mg/l. L-leucine, 10 mcg/l. D-giotin, and 200 mcg/l. Thiamine.HCl.

TABLE 8

| Gelatin Liquefaction | |
|---|---|
| Culture | Liquefaction |
| CBS 599 | + |
| CBS 6124 | + |
| ATCC 20228 | + |
| ATCC 20628 | + |
| ATCC 20688 | + |
| PC-30869 | − |

The medium contained 120g/l gelatin and 16.7 g/l. Bacto-Vitamin-free yeast Base plus 100 mg/I. uracil, 100 mg/l. L-leucine, 10 mcg/I. D-biotin, and 200 mcg/l Thiamine.HCl.

BRIEF DESCRIPTION OF THE DRAWINGS

FIG. 1 - Partial linear restriction map of overlapping plasmids pLD 57, pLD 58 and pLD 62 isolated from *Y. lipolytica* strain DL112.

FIG. 2 - Synthetic oligonucleotide probes for the XPR2 gene. From the published sequence for most of the first 25 amino acid residues of the mature protease (Ogrydziak et al., loc. cit.), two regions labeled I and II) offer the possibility for constructing 14-mer ologonucleotide probes with 32-fold or less degeneracy. The two regions begin at amino acids 7 and 18, respectively. Four different eight-fold degenerate mixed probes were prepared for each region and assigned numbers between 170 and 186 as shown. In the predicted nucleic acid sequences shown, "X" means all 4 bases, "U" means both purines and "Y" means both pyrimidines.

FIG. 3 - Nucleotide sequence of XPR2 gene showing promoter, pre (-157 to -136), pro1 (-135 to -98), pro2 (-97 to -1), alkaline extracellular protease and terminator sequences.

FIG. 4 - Construction sequence for terminator vector pterm 4.

FIG. 9 - Amino acid sequence of human anaphylatoxin C5a.

FIG. 11 - Construction sequence and restriction map of plasmid pC5aX-3.

FIG. 12 - Nucleotide sequence of the LEU2 gene.

SEQUENCE ANALYSIS OF THE XPR2 GENE

Figure 5:
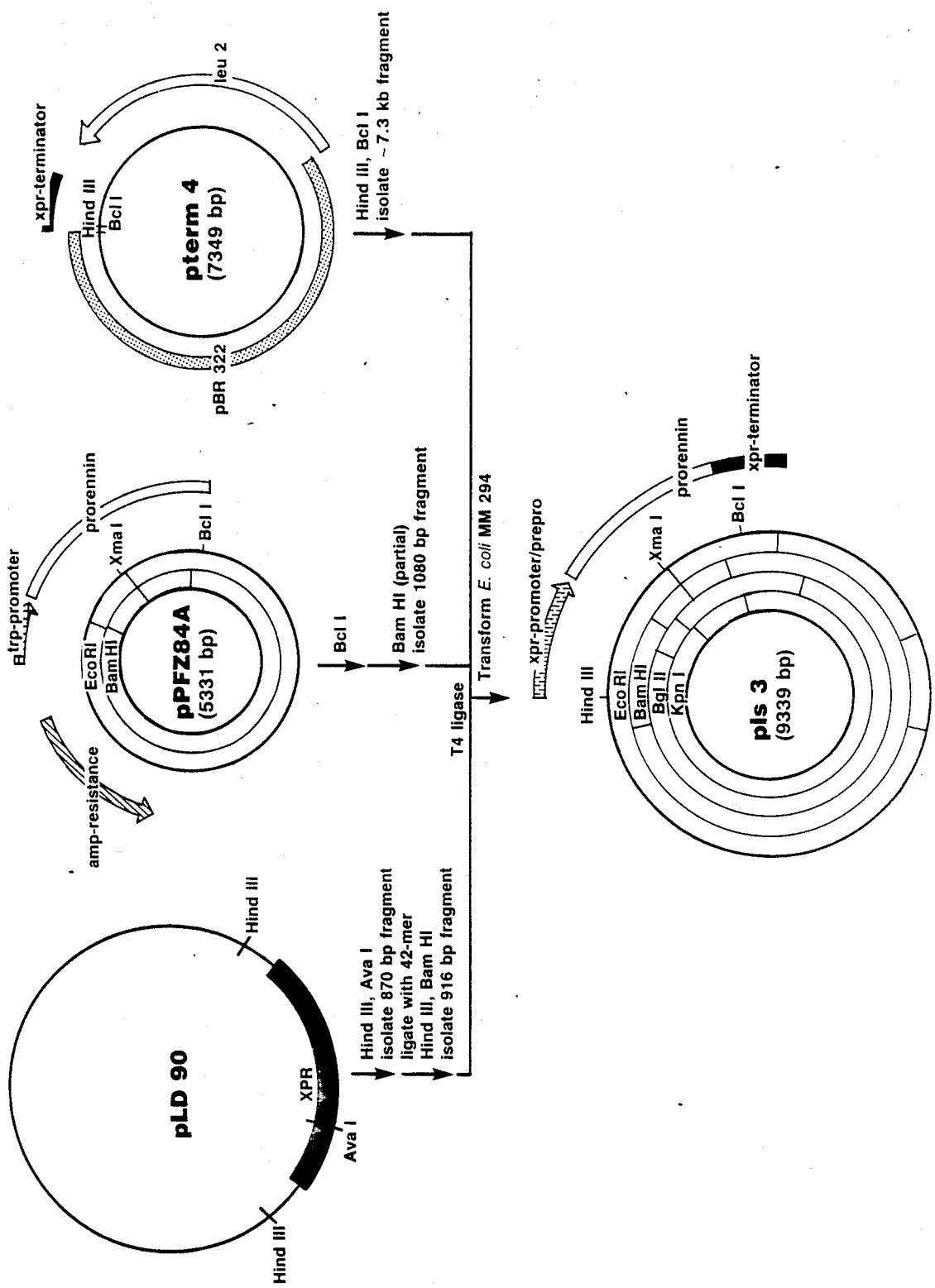
FIG. 5 - Construction sequence and restriction map of plasmid pLS-3.

DNA sequence analysis of the cloned XPR2 gene was performed by the chemical degradation method (Maxam et al. 1980, Methods Enzymol. 65, 499) on overlapping restriction fragments prepared from plasmids pLD57, pLD58, pLD62 (FIG. 1) and pLD84 and pLD86 (see below). The results showed that the cloned yeast genomic DNAs indeed contained the gene for the exocellular alkaline protease. The nucleotide sequence of the XPR2 gene and the amino acid sequence of the alkaline protease precursor with its signal sequence as deduced from the nucleotide sequence are shown in FIG. 3. A large portion of the amino acid sequence of the exocellular protease was unknown (Ogrydziak et al., loc. cit.) and is presented here for the first time. Furthermore, the sequences required for expression and secretion of the exocellular protease are described here for the first time. The DNA sequence coding for the alkaline protease, its precursor and signal sequences consists of 1362 base pairs (FIG. 3). The primary structure of this polypeptide chain was deduced from the nucleotide sequence to be 454 amino acid residues. The alkaline protease is synthesized in the cell in a precursor form which is proteolytically processed to the secreted or mature form. Analysis of the N-terminal amino acid sequence deduced from the nucleotide sequence revealed the existence of a putative signal peptide in the precursor molecule. Said signal peptide contains 22 amino acid residues and its structural features are similar to those of higher eukaryotic and prokaryotic signal peptides (Perlman et al., 1983, J. Mol. Biol. 167, 391). A region in the predicted amino acid sequence in general agreement with the known 25 N-terminal amino acids of the mature alkaline protease (Ogrydziak et al., 1982, J. Gen. Microbiol. 128, 1225) was preceded by 157 amino acid residues containing the signal peptide and two trypsin-type cleavage sites (Lys-Arg). Said cleavage sites were used to divide the pro region into pro1(-135 to -98) and pro2 (-97 to -1). See FIG. 3. The mature alkaline protease has 297 amino acids as deduced from the nucleotide sequence. The amino acid sequences predicted for the various forms of protease from the nucleotide sequence are consistent with the sizes of the purified forms of the enzyme. In addition to the alkaline protease precursor structural sequence, approximately 700 bp of 5'-flanking sequence and 600 bp of 3'-flanking sequence were determined. Analyses of these regions demonstrated they contain sequences analogous to other eukaryotic promoters and terminators, and are likely essential for alkaline protease expression.

As mentioned above, methodology for transforming Y. lipolytica and for cloning Y. lipolytica genes by complementation of mutations, including cloning of the XPR2 gene, which codes for a secreted alkaline protease, by complementation of an xpr2 mutation are reported in EP 0138508. The procedure described therein includes transforming a Y. lipolytica host strain with a BglII partial digest of a Y. lipolytica gene library in vector pLD40, said vector characterized by the fact it harbors a small segment containing the LEU2 region of Y. lipolytica, and 3EcoRI, 4EcoRV, 6AvaI, 1BglII, 1NcoI, 1ApaI, 2XhoI and 1BstXI endonuclease restriction sites. One of the Y. lipolytica XPR2 transformants was used to recover the wild type gene (pLD84 and pLD86) from Y. lipolytica NRRL Y-1094 for use in expression/-secretion vector construction as described in Example 1.

Sequence Analysis of the LEU2 Gene. DNA sequence analysis of the cloned LEU2 gene in pLD25 (EP 0138508) was determined by the chemical degradation method (Maxam et al. 1980, Methods Enzmol. 65, 499) on overlapping restriction fragments. To locate the beta-isopropylmalate (IPM) dehydrogenase coding region and proper reading frame, advantage was taken of the predicted amino acid sequence previously determined for the LEU2 gene of S. cerevisiae (Andreadis et al., 1984, J. Biol. Chem. 259, 8059). The region of the Y. lipolytica genomic sequence which encodes an amino acid sequence homologous to a region of the S. cerevisiae protein sequence was identified. The nucleotide sequence of the 2.8-kb LEU2 gene and the amino acid sequence of beta-IPM dehydrogenase as deduced from the nucleotide sequence are shown in FIG. 12. Furthermore, the sequences required for expression of the Y. lipolytica beta-IPM dehydrogenase are described here for the first time. The DNA sequence coding for this 405 amino acid protein consists of 1215 base pairs (FIG. 12). In addition to beta-IPM dehydrogenase coding sequence, approximately 798 bp of 5' flanking sequence and 797 bp of 3'-flanking sequence (including the TAA translation termination codon) were determined. Analyses of these regions demonstrated they contain sequences analogous to other eukaryotic promoters and terminators, and are essential for expression.

The 5'-upstream region of the Y. lipolytica LEU2 gene contains a TATATATA sequence 78 bp in front of the translational start and 30 bp in front of the proposed mRNA start. A second sequence important for transcription initiation in eukaryotes is the CAAT box which, in the LEU2 gene, is located 74 bp in front of the presumed transcription initiation site which is -48 bp from the ATG (FIG. 12).

The 3'-downstream region has a sequence at 72 to 120 nucleotides after the stop codon (TAA) homologous to the 5'-TAG ... TA(T)GT ... TTT-3' sequence proposed by Zaret et al., Cell 28, 563 (1982) as important for transcription termination in S. cerevisiae.

EXAMPLE 1 strain used was ATCC 20774 (MATB leu2-40 bio-6 xpr2-1002). The XPR2 transformant, Y. lipolytica ATCC 20781, was discovered as a colony that formed a zone on skim milk indicator plates, following replica plating from leucine-deficient plates. Chromosomal DNA was prepared from the transformant by the method of EP Application No. EP 0138508 and used to recover the gene for the secreted protease. The chromosomal DNA was partially digested with BglII enzyme, ligated to circularize the fragment containing both the E. coli replicon and ampicillin-resistance gene from the vector, and used to transform E. coli. The chromosomal DNA was also digested with SalI enzyme and used in a Southern experiment which indicated that the normal LEU2 region of the transformant was not perturbed. (A 520 bp SalI to Eco RI segment of the LEU2 region just 5' to the segment of LEU2 contained in pLD40 was used as the probe). Therefore, since homology is necessary for the integration of a library plasmid into Y. lipolytica, the XPR2 region must have been the site of integration. Three overlapping but different plasmids, pLD57, pLD58 and pLD62, were initially recovered from Y. lipolytica ATCC 20781. They are shown in FIG. 1. Hybridizations with synthetic oligonucleotide probes for the XPR2 gene, based on the known sequence of the first 25 amino acid residues of the mature secreted protease protein (FIGS. 2 and 3), showed that the gene for the secreted protease had been cloned. To determine whether the recovered gene represented the wild type copy or the mutant copy, the recipient *Y. lipolytica* strain was transformed with pLD58. Since no protease positive transformants resulted from any leucine-independent transformants, it was concluded that pLD58 contained the mutant allele of the gene.

The form of the XPR2 gene present in the wild type strain NRRL Y-1094, was obtained by an *E. coli* colony hybridization experiment. As a probe, the 2 kb PvuI to EcoRI fragment predicted from sequencing data to contain the entire structural gene was used. From the original library of Sau3A partial-digest fragments of NRRL Y-1094 DNA in pLD40, described in EP application 0138508, several colonies that hybridized to the probe were obtained. Two of these colonies contained the very similar plasmids designated pLD84 and pLD86, which were used to develop expression vectors. Both plasmids contain the same 5' end of the XPR2 region—the Sau3A site (that was joined to and regenerated the BamHI site of the vector) from which the 5' sequence begins in FIG. 3. Each contain all of the structural gene for the protease and the presumed transcription terminator and include approximately 4 to 5 kb total insert from the XPR2 region of strain NRRL Y-1094. The insert in pLD86 contains a few hundred base pairs extra at the 3' end. Since we used the 3' extent as far as the BglII site (base pair 2655) for expression vector construction, the two plasmids supplied the same DNA that was functionally identical in sequence to FIG. 3.

Construction of Expression/Secretion Vectors. The plan devised to achieve expression and secretion of prorennin in *Y. lipolytica* employs the construction of various hybrid genes in an integrative cloning vector. Such an approach creates several different plasmids that share extensive regions of common DNA sequences. In fact, a modular construction scheme was used to assemble vectors with the prorennin gene inserted 3' to the predicted XPR2 signal peptide processing site, the presumed pro1- processing site, and the cleavage site known to generate the mature alkaline protease. In general, it is desirable for the heterologous gene to be inserted between yeast promoter and terminator sequences for expression. It was recognized that the N-terminal portion of the hybrid gene sequences will vary in the different plasmid constructions, but the prorennin structural gene sequence, the XPR2 terminator sequence, and the shuttle vector DNA would be the same in each expression plasmid construction. It was planned that the same prorennin structural gene fragment and the terminator/vector plasmid would be used in each expression plasmid construction, as described below. The different prorennin expression/secretion plasmid constructions vary in the region immediately downstream from the XPR2 gene promoter sequence in the length of the N-terminal alkaline protease precursor sequence that precedes the prorennin gene sequence. Therefore, the promoter fragment component of each expression plasmid was designed to be the variable sequence in the region of the XPR2-prorennin junction. All expression/secretion vectors were assembled by a similar ligation reaction containing three component fragments.

The experimental steps used for constructing the terminator vector pterm 4, are shown in FIG. 4. First a synthetic linker was ligated to a fragment containing the 3' end of the XPR2 gene, including the transcription termination and polyadenylation signals. Briefly, the plasmid pLD84 was cleaved with the endonuclease KpnI and ligated with the synthetic double-stranded linker DNA shown in FIG. 4. The ligation product was cleaved with endonucleases HindIII and BglII and a 760 base pair fragment was inserted into plasmid pLD41 linearized with the same two endonucleases to yield pterm 4. Plasmid pterm 4 was identified by its restriction map. The results of a series of restriction endonuclease digestions using EcoRV, EcoRI, KpnI, BglII-HindIII, and BglII-BclI were analyzed. The digestions provide suitable fragments that confirm the presence of the synthetic linker and the "complete" 3'-end of the XPR2 gene in shuttle plasmid pLD41, described in EP 0138508. A partial map of this 7.3 kb terminator vector is shown in FIG. 4.

Construction of the Expression/Secretion Plasmid pLS-3. FIG. 5 outlines the construction of the initial plasmid used for secretion of prorennin in *Y. lipolytica*. Its restriction map is presented in FIG. 5. The construction of the prorennin secretion plasmid was initiated by preparing a fragment containing most of the prorennin structural gene sequence. The 1080 base pair BclI-BamHI (partial) DNA fragment containing the coding sequence for prorennin residues 6 to 365 was isolated from *E. coli* prorennin expression plasmid pPFZ-84A. (Plasmid pPFZ-84A is a derivative of prorennin expression plasmid pPFZ-R2, the construction of which is described in EP application No. 0147178, published July 3, 1985 and was generated by synthetic oligonucleotide directed mutagenesis employing restriction fragment replacement. Specifically, pPFZ-84A differs from pPFZ-R2 by only two base pairs at prorennin amino acid residues 214 (Asn→Asp) and 286 (Asp→Gly), so as to encode the so-called prorennin A allele, however, both plasmids contain the desired sequence for prorennin and are functionality equivalent in this example). The XPR2 promoter component fragment, containing coding sequences for alkaline protease precursor 1 to 157 and prorennin 1 to 5, was prepared as follows. The 870 base pair HindIII-AvaI DNA fragment containing the promoter region and the 5' end of the alkaline protease gene was isolated from the XPR2 subclone plasmid pLD90. This fragment was ligated with a synthetic fragment which has the structure:

```
5' CCGAGATTCCTGCTTCTTCTAATGCCAAGCGAGCTGAGATCACTAG    3'
3'    CTAAGGACGAAGAAGATTACGGTTCGCTCGACTCTAGTGATCCTAG 5'
```

This sequence contains an AvaI cohesive terminus, followed by sequences coding for the last nine codons of the alkaline protease pro-peptide, followed by sequences coding for the first four amino acids of prorennin, and terminates in a BamHI site. The promoter component fragment was created by a standard ligation reaction utilizing the synthetic fragment and the 870 bp HindIIIAvaI fragment with T4 ligase followed by cleavage with HindIII and BamHI. The resulting ligated sequences were purified by polyacrylamide gel electrophoresis selecting for the appropriate 916 base pair HindIII-BamHI DNA fragment. The 3'-end of the hybrid gene was obtained from the terminator/vector plasmid pterm 4, described above. Plasmid pterm 4 was digested with HindIII and BclI and the approximately 7.3 kb HindIII-BclI terminator/vector DNA fragment, containing the XPR2 terminator, LEU2 selectable marker, and pBR322, was isolated from an agarose gel.

The prorennin expression/secretion plasmid pL,S-3 was assembled by incubating the three component DNA fragments (HindIII-BclI cleaved pterm 4 plasmid, along with the 916 bp HindIII BamHI promoter and 1080 bp BamHI-BclI prorennin gene containing fragments), constructed as described above in the presence of T4 ligase (see FIG. 5). The ligation mixture was used to transform E. coli K12 strain MM294 via the CaCl2 method of Dagert et al., Gene 6, 23–28 (1979). Plasmids were isolated from the ampicillin resistant selected transformants, and plasmid pLS-3 was identified by its restriction map (FIG. 6A). The XPR2-prorennin region of this plasmid was sequenced to confirm the proper sequence of the synthetic DNA and the proper junction of the desired fragments.

Preparation of pLD90—This plasmid contains a subclone from pLD84. A region of DNA from the PvuI site in the promoter region of XPR2 to the EcoRI site in the terminator region was subcloned into the HindIII site of pBR322 as follows. Several micrograms of pLD84 were digested with the two restriction enzymes named above. Then the "sticky" ends of the digested DNA molecules were filled in with the Klenow fragment of DNA polymeraseI. Then kinased HindIII linkers (CAAGCTTG from New England Biolabs) were added onto the ends with T4 DNA ligase. Excess linkers were removed and sticky HindIII ends were generated by subsequent digestion with HindIII enzyme. The mixture of DNA molecules was run on a preparative agarose gel, and the desired 2 kb band was cut out, purified and added to a ligation reaction with HindIII-digested, bacterial alkaline phosphatase treated vector pBR322. The ligation mixture was used to transform competent E. coli. The orientation with the EcoRI site of the XPR2 terminator closer to the EcoRI site of pBR322 was named pLD90 and the reverse orientation was named pLD91.

The 5' extreme of the XPR2 promoter region that was included in pLS-3 is the PvuI site, approximately 280 bp in from the beginning of the area sequenced in FIG. 3. It was found that plasmids containing the wild type protease gene under the control of only this much of the promoter, when integrated into the genome at a site away from the resident xpr2 locus, did not enable the transformant to make large quantities of protease (judged by zones of clearing on skim milk plates).

We noted that if pLS-3 contained a shortened, and thereby "deficient" promoter, then an integrant resulting from recombination between the plasmid and a resident wild type XPR2 gene would yield a complete promoter directing expression of the prochymosin fusion product but a deficient promoter directing protease expression. An analogous gene disruption-type experiment was performed with the S. cerevisiae actin gene by Shortle et al. (Science 217:371–373 1982). In agreement with our expectations, some leucine-independent transformants with pLS-3 were, in fact, now protease deficient. The protease deficient transformants were more likely to be the desired integrants at the XPR2 locus than the unwanted by-products such as gene convertants at leu2. With recipient strain ATCC 20688, we found that uncut pLS-3 generated 6.5% protease-deficient transformants, whereas SnaBI-cut plasmid yielded approximately 70% protease-deficient transformants. The gene disruption aspect of this transformation was used to by-pass the need for a large number of Southern blot experiments to find the correct integrant among all the transformants.

Plasmids containing the wild type protease structural gene under control of the XPR2 promoter (beginning as sequenced in FIG. 3) allow expression of significant amounts of protease when integrated into Y. lipolytica cells at a site other than the xpr2 locus. However, efficient expression of heterologous genes from these sorts of integrants may require further modification of this control region DNA.

Secretion of Prorennin. Y. lipolytica strain ATCC 20688 was transformed with uncut pLS-3 DNA and SnaBI digested pLS-3 DNA to obtain xpr− leu+ transformants ATCC 20775 (DL144) and ATCC 20776 (DL148), respectively. These transformant strains were inoculated into a test tube containing YEPD medium. The cells were grown overnight at 28° C. An aliquot (250 ul) of these cultures was diluted 1:100 into 25 mls of GPP medium. The cells were grown in shaker flask at 28° C. for 16–18 hours, to a resulting absorbance at 600 nm of 5.0–7.0, and harvested by centrifugation. The resulting culture fluid or supernatant was assayed for the presence of prorennin by concentrating the supernatant and subjecting the concentrate to SDS-PAGE. The slab gel was electrophoretically transferred to nitrocellulose paper in the presence of 20 mM Tris Base, 150 mM glycine, 20% methanol at 500 m amp for 2 hours at 4° C. Removal of the protein from the slab gel was verified by staining with Coomassie blue.

The nitrocellulose paper was dried at 37° C. and baked at 65° C. for 1 hour, then washed in TBS (200 mM NaCl, 50 mM Tris-HCl pH 7.5). The paper was then incubated at room temperature for 30 minutes in TBS containing 10% horse serum (Gibco, Chagrin Falls, Ohio) followed by incubation in TBS containing 10% horse serum and an appropriate dilution of prorennin antibody for 16 hours at room temperature. The paper was then washed three times for 10 minutes in TBS, followed by incubation in TBS containing 10% horse serum, followed by incubation for 2 hours in TBS containing 10% horse serum and an appropriate dilution of goat anti-rabbit IgG antibody conjugated to horseradish peroxidase. The paper was then washed three times for 10 minutes in TBS and developed in the presence of 4-chloro-1-naphthol (3 mg/ml. in methanol), added to a concentration of 0.5 mg/ml., in TBS containing 0.01% hydrogen peroxide. The presence of prorennin at a molecular weight of 40,000 was confirmed in both supernatants.

After acid activation of concentrated culture supernatants (see above), significant milk clotting activity was present in the samples prepared from transformant cultures ATCC 20775 and 20776 containing pLS-3. As expected, no milk clotting activity was obtained in the control culture supernatant of recipient strain Y. lipolytica ATCC 20688.

Construction of Expression/Secretion Plasmid pXX-33. Modification to convert pLS-3 into an improved expression plasmid pXX-33 is outlined in FIG. 6. Such modification increased the XPR2 promoter region by 280 bp. As in the case of pLS-3, the expression plasmid pXX-33 contains a hybrid gene coding for the entire prepro-peptide (157 amino acid residues) of alkaline protease joined to the entire structural gene sequence of prorennin.

Before constructing the prorennin expression/secretion plasmids with 280 bp more of the XPR2 promoter sequence than in pLS-3, it was necessary to subclone a restriction fragment containing the entire alkaline protease gene into a HindIII site. This subclone was assembled by adding synthetic linkers to a restriction fragment isolated from the XPR2 genomic library clone pLD86. The construction of this XPR2 subclone with an upstream HindIII site was initiated by preparing a DNA fragment containing all of the alkaline protease gene. The 2.3 kb EcoRI-BamHI (partial)fragment from the genomic region of the XPR2 clone pLD-86 was purified by agarose gel electrophoresis, and ligated with a synthetic fragment which has the sequence

```
5' GATCGAAGCTTG      3'
3'       TTCGAACTTAA 5'
```

This linker sequence contains a BamHI cohesive termini (but does not regenerate the BamHI site), followed by a HindIII site, followed by an EcoRI sticky end. The ligation product was digested with HindIII and inserted into the HindIII site of pBR322. The plasmid pXHP-24 was identified by its restriction map and became the source of the XPR2 promoter fragments for future expression constructions.

Figure 6:
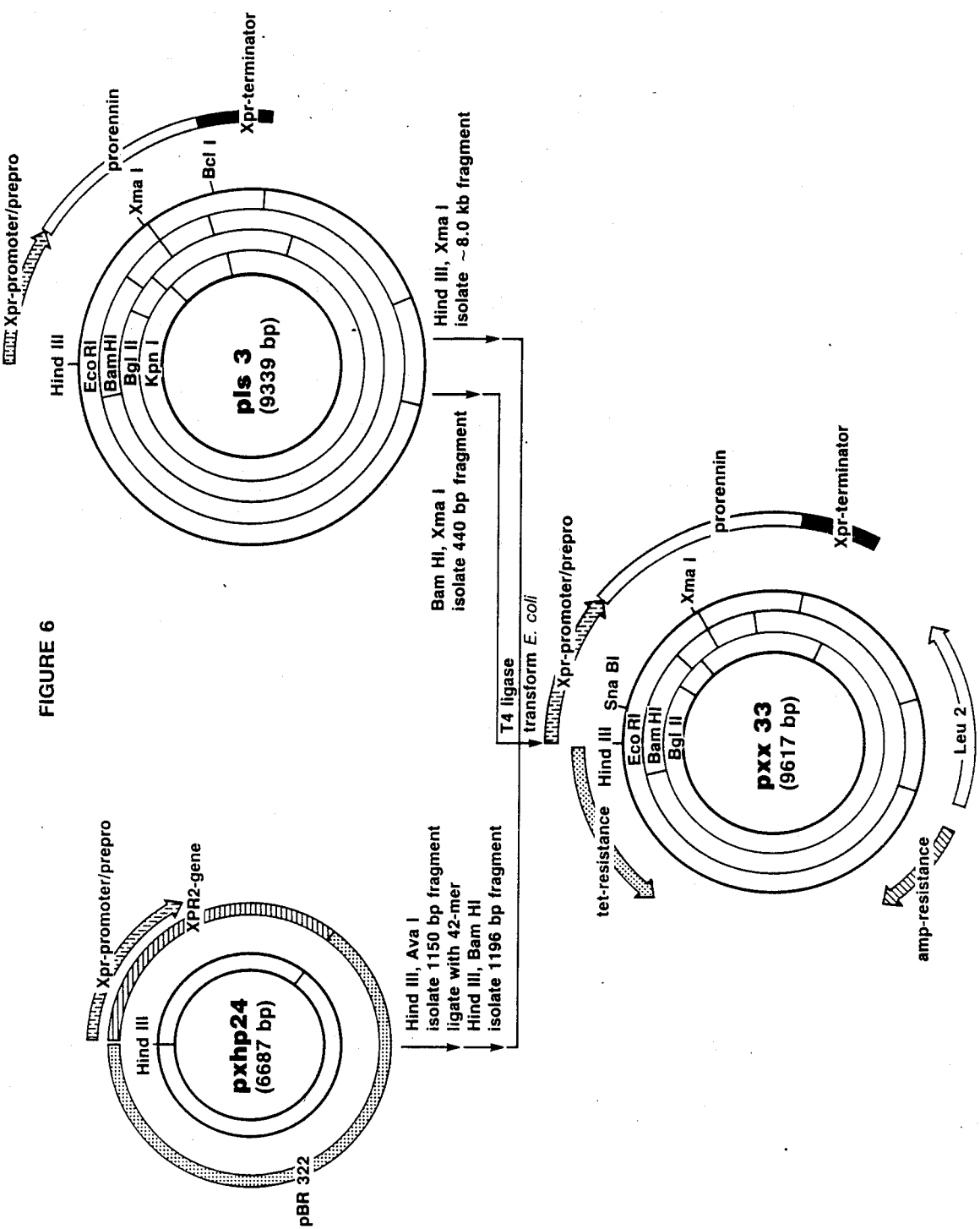
FIG. 6 - Construction sequence and restriction map of plasmid pXX-33.

In plasmid pXHP-24 the subcloned XPR2 gene contains approximately 280 base pairs more of 5' XPR2 promoter sequence than the XPR2 promoter sequence contained in pLS-3. First, the promoter component fragment was created by a standard ligation reaction utilizing the synthetic DNA fragment (described above for pLS-3) and the 1150 base pair HindIII-AvaI fragment from pXHP-24 with T4 ligase followed by cleavage with HindIII and BamHI. The resulting ligated sequences were purified by gel electrophoresis selecting for the approximately 1196 base pair HindIII-BamHI fragment. A second fragment containing sequences coding for prorennin amino acid residues 6 to 151 was prepared from pLS-3 by cleavage with BamHI and XmaI, and gel purification of the resulting 440 base pair BamHI-XmaI DNA fragment. A third fragment containing the rest of the prorennin gene, the XPR2 terminator, and vector sequences was prepared from pLS-3 by cleavage with HindIII and XmaI, and gel purification of the approximately 8.0 kb HindIII-XmaI vector fragment. The three fragments were then ligated using the standard procedure described above. The ligation reaction was used to transform E. coli K12 strain MM294. Plasmids were isolated from the transformants selected on the basis of ampicillin resistance, and plasmid pXX-33 was identified by its restriction map (FIG. 6). The protease-prorennin region of this plasmid was sequenced to confirm the proper junction of the desired fragments.

Y. lipolytica ATCC 20774 was then transformed with SnaBI cleaved pXX-33 to provide Y. lipolytica ATCC 20780 and the prorennin secreted into the culture broth by the transformed cultures assayed as described above in the case of pLS-3. The presence of prorennin in the culture supernatant was confirmed.

After acid activation of concentrated culture supernatants (see above), significant milk clotting activity was observed in the samples prepared from the transformed culture Y. lipolytica ATCC 20780.

Figure 7:
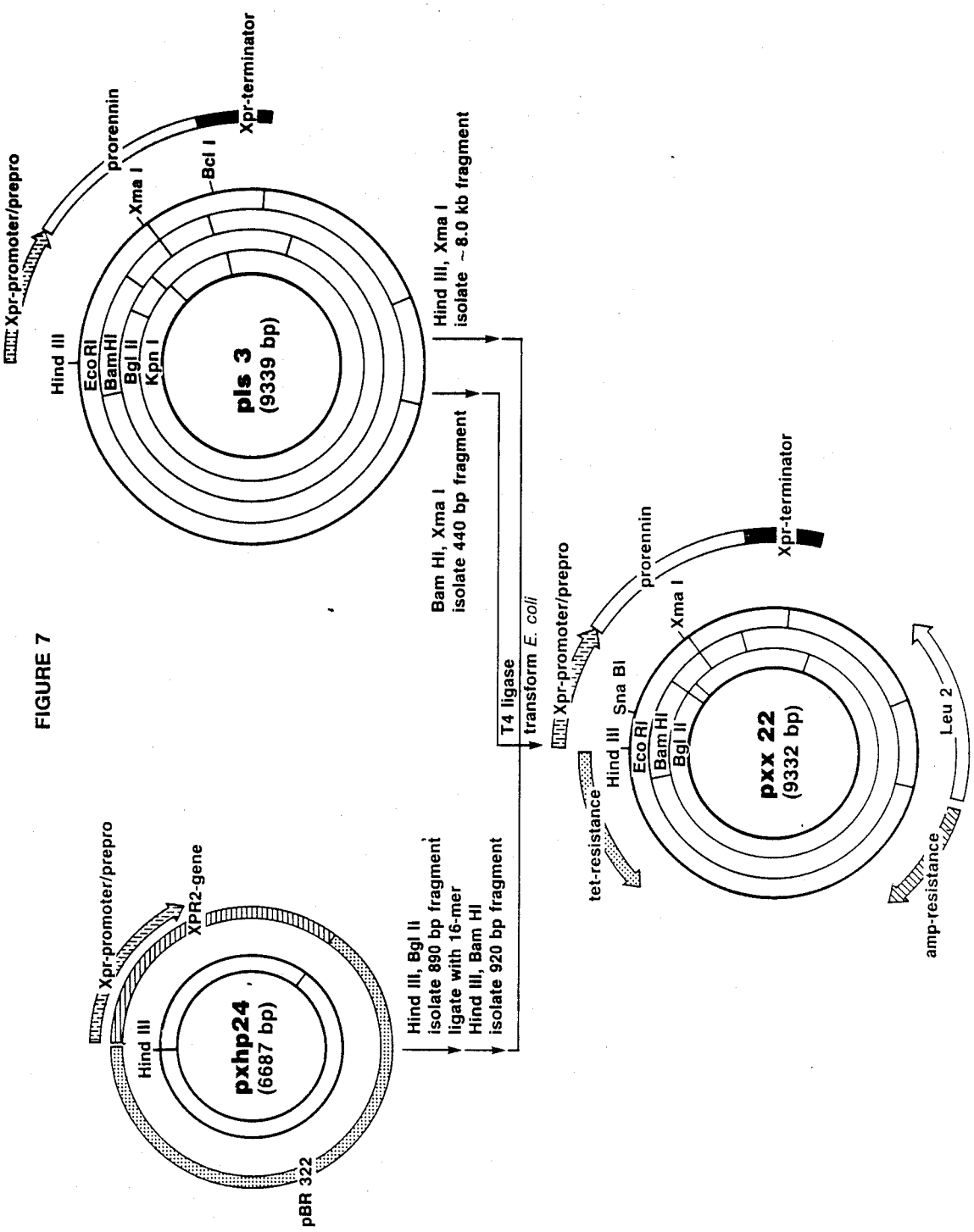
FIG. 7 - Construction sequence and restriction map of plasmid pXX-22.

Construction of Expression/Secretion Plasmid pXX-22. The experimental steps used for constructing the expression/secretion plasmid pXX-22 are shown in FIG. 7 The expression vector differs from pLS-3 in two respects. Like pXX-33, it contains the additional 280 bp segment XPR2 promoter sequence. Second, it contains the sequence encoding the alkaline protease signal peptide and only 38 amino acid residues of the pro-peptide (pro1).

The construction plan for pXX-22 was analogous to that used for pXX-33. First, the promoter component fragment was created by a standard ligation reaction utilizing the 890 base pair HindIII-BglII fragment from pXHP-24 and the synthetic fragment with the sequence

```
5' GATCTTGCTGAGATCACTAG     3'
3'      AACGACTCTAGTGATCCTAG 5'
``` with T4 ligase followed by digestion with HindIII and BamHI. The resulting ligated sequences were purified by gel electrophoresis isolation of the 920 base pair HindIII-BamHI DNA fragment. A second fragment coding for prorennin residues 6 to 151 was isolated from pLS-3 by cleavage with BamHI and XmaI, and gel purification of the resulting 440 base pair BamHI-XmaI DNA fragment. A third fragment containing the rest of the prorennin gate, XPR2 terminator, and vector sequences was prepared by cleavage of pLS-3 with HindIII and XmaI, and gel purification of the approximately 8.0 kb vector fragment. Then the three DNA fragments were ligated using the standard procedure described above. The ligation reaction was used to transform E. coli K12 strain MM294. Plasmids were isolated from the selected transformants, and plasmid pXX-22 was identified by its restriction map (FIG. 7).

Y. lipolytica ATCC 20774 was then transformed with SnaBI cleaved pXX-22 to provide Y. lipolytica ATCC 20779 and the prorennin secreted into the culture broth by the transformed cultures assayed as described above in the case of pLS-3. The presence of prorennin in the culture supernatant was confirmed according to the procedure described above. After acid activation of concentrated culture supernatants (see above), significant milk clotting activity was observed in the samples prepared from the transformed culture Y. lipolytica ATCC 20779.

Construction of Expression/Secretion Plasmid pXX-11. The experimental steps for constructing the prorennin expression/secretion plasmid pXX-11 are outlined in FIG. 8. This plasmid contains the sequence for the XPR2 promoter and the 22 amino acid residue signal peptide joined to the sequence coding for prorennin. The construction plan used for pXX-11 was similar to that used for pXX-22 and pXX-33. Briefly, the promoter component fragment was created by a standard ligation reaction utilizing the approximately 750 base pair HindIII-BglII DNA fragment from pXHP-24 and the synthetic fragment with the sequence

Figure 8:
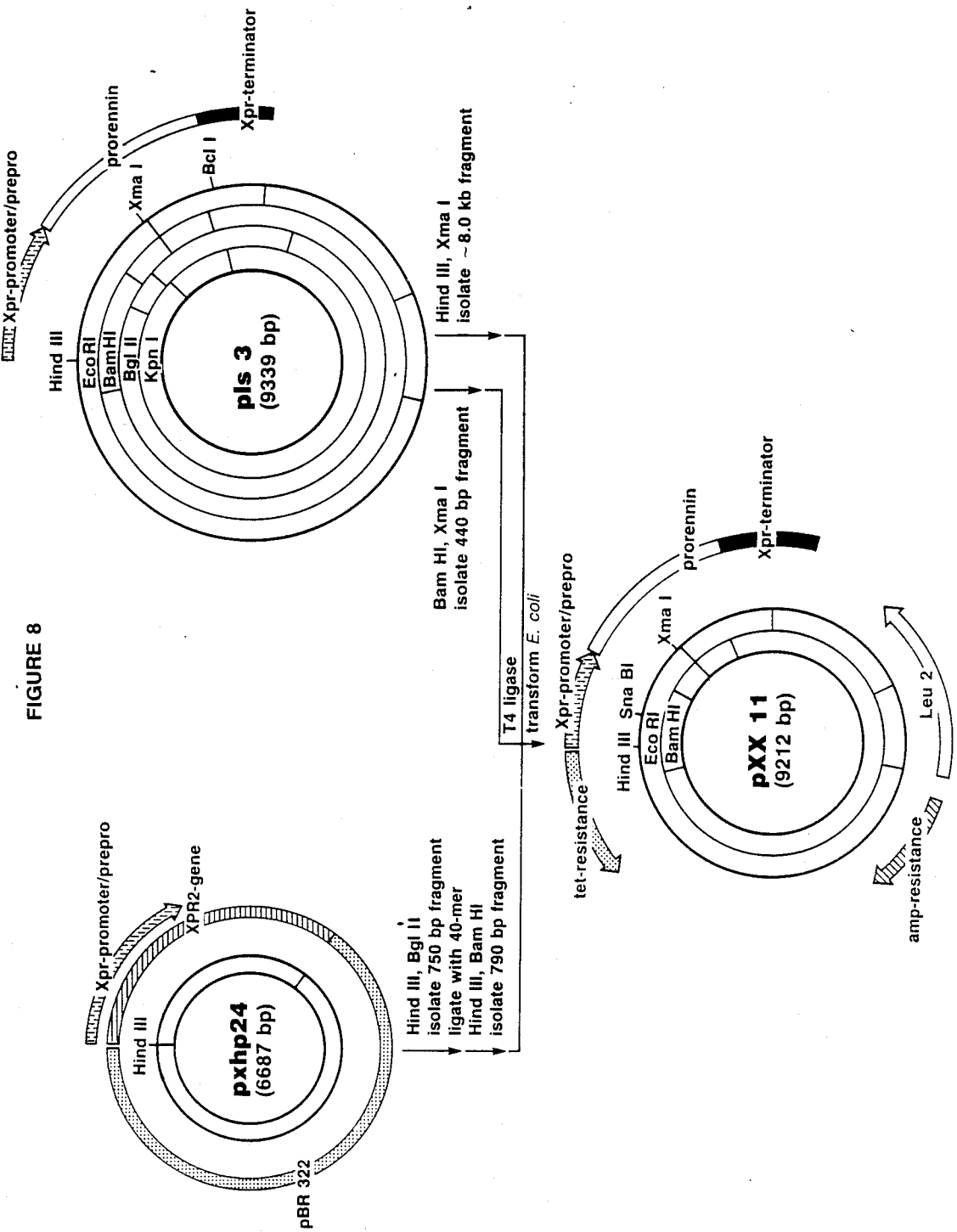
FIG. 8 - Construction sequence and restriction map of plasmid pXX-11.

```
5'     TGGCCGCTCCCCTGGCCGCCCCTGCCGCTGAGATCACTAG        3'
  3'AAGACCGGCGAGGGGACCGGCGGGGACGGCGACTCTAGTGATCCTAG 5' ——>
``` with T4 ligase followed by cleavage with HindIII and BamHI. The resulting ligated sequences were purified by gel electrophoresis selecting the 790 base pair HindIII-BamHI DNA fragment. A second fragment coding for prorennin residues 6 to 151 was isolated from pLS-3 by cleavage with BamHI and XmaI, and gel purification of the resulting 440 base pair BamHI-XmaI DNA fragment. A third fragment containing the remainder of the prorennin structural gene, XPR2 terminator, and shuttle vector sequences was prepared by cleavage of pLS-3 with HindIII and XmaI, and gel purification of the approximately 8.0 kb vector fragment. Then the three DNA fragments were ligated using the standard procedure described above. The ligation reaction was used to transform *E. coli* K12 strain MM294. Plasmids were isolated from the selected transformants, and plasmid pXX-11 was identified by its restriction map (FIG. 8). The XPR2-prorennin portion of this plasmid was sequenced to confirm the proper sequence of the synthetic DNA and the proper junction of the desired fragments.

*Y. lipolytica* ATCC 20774 was then transformed with SnaBI cleaved pXX-11 to give *Y. lipolytica* 20778 and the prorennin secreted into the culture medium by the transformed cultures was assayed as described above in the case of pLS-3. The presence of prorennin in the culture supernatant was confirmed according to the procedure described above.

Milk clotting assays (see above) showed there was significant milk clotting activity in the culture supernatant of transformants ATCC 20778 containing pXX-11.

EXAMPLE 2

Construction of the Docking Platform

The wild type BIO gene corresponding to the bio-6 allele in ATCC 20774 was cloned by complementation as follows. A gene library of partially Sau3A-digested *Y. lipolytica* chromosomal DNA inserted into the BamHI site of pLD40 (which is pBR322 plus LEU2 at the EcoRI site) was constructed and a large quantity of library DNA prepared as a mixed-culture *E. coli* plasmid preparation (This is the same library as was used to clone the XPR2 gene). Several micrograms of the library DNA was digested with the enzyme ApaI (which cuts once in the LEU2-region). Then, this DNA was used to transform ATCC 20774 (leu2 xpr2 bio), with the transformation mixture being plated out on synthetic medium lacking leucine. Tens of thousands of leucine-independent transformants were obtained. To find which, if any, colonies contained library plasmids that included the BIO gene, the leucine independent transformants were replica plated to agar plates containing biotin selection medium (recipe per L: 25 mg desthiobiotin, 20 g glucose, 5 g ammonium sulfate, 1 g $KH_2PO_4$, 0.5 g $MgSO_4.7H_2O$, 0.1 g, $CaCl_2$, 0.1 g, NaCl, 500 ug boric acid, 400 ug thiamine.HCl, 400 ug $ZnSO_4.7H_2O$, 400 ug $MnSO_4.H_2O$, 200 ug $Na_2MoO_4.2H_2O$, 200 ug $FeCl_3.6H_2O$, 100 ug KI and 40 ug $CuSO_4.5H_2O$).

One of several *Y. lipolytica* BIO+ transformants to grow on biotin selection medium was named DL31. We then proceeded to recover the gene library plasmid containing the BIO gene from *Y. lipolytica* strain DL31. Chromosomal DNA was prepared from a culture of strain DL31. A few micrograms of this chromosomal DNA was digested with the restriction enzyme ApaI to excise the library plasmid. An aliquot of the digested DNA was used in a ligation reaction to circularize the unknown library plasmid. The ligation mixture was then used to transform an *E. coli* culture for ampicillin resistance to recover the unknown BIO-containing plasmid into *E. coli*. A few *E. coli* ampicillin-resistant transformants were obtained. Small scale plasmid preparations were done on the *E. coli* transformants. Restriction digests of the plasmid DNA thus obtained revealed that the unknown BIO-containing plasmid, as expected, was equivalent to pLD40 with an insert into the BamHI site. This plasmid must have come originally from our gene library and was named pLD51.

The plasmid pLD56 was generated as a subclone of pLD51 by removal of the LEU2 gene from pLD51, as follows. An aliquot of plasmid pLD51 was digested with the enzyme EcoRI to remove the LEU2 region. The digested DNA was used in a DNA ligation reaction to recirculate the plasmid. Then an *E. coli* transformation was performed to clone the smaller BIO-containing plasmid. One of the ampicillin-resistant *E. coli* transformants was shown to contain the expected smaller plasmid, which was named pLD56. Several restriction digests of pLD56 were performed. The BIO-containing segment of pLD56, which occurs as an insert at the BamHI site of pBR322, was approximately 3.6 kb long.

A very rough restriction map of the 3.6 kb insert of *Y. lipolytica* DNA into the BamHI site of pBR322 (comprising pLD56) is described below with the approximate distance in base pairs from the beginning of the insertion indicated in parentheses. The size estimates were made from a few agarose gels and are subject to relatively large quantitative errors: PvuII (800), PvuII (1200), PstI (1800), MluI (2000), PstI (2300), EcoRV (2700), NcoI (3200) (For orientation, the SalI site of pBR322 would precede the sites described and the HindIII site would follow them).

Strain ATCC 20774 (MATB leu2-40 bio-6 xpr2-1002) was transformed with intact pID56 (pBR322 plus approximately 3.6 kb of *Y. lipolytica* chromosomal DNA containing the BIO gene). Three different biotin-independent transformants were tested for high frequency transformation of NruI-cut (targeted to pBR322) pLD40 (LEU2 on pBR322) relative to the parent strain to determine which contained a resident pBR322 integrated into the BIO-region. All three showed high frequency transformation because of integration of the pLD40 into the resident pBR322. This was confirmed by Southern blot hybridization experiments. One of the three original *Y. lipolytica* BIO transformants was named DL118 and used further as a DNA recipient. The restriction map above was needed to determine (i) what to use as a BIO-specific hybridization probe (an NcoI-PvuII piece), (ii) which enzyme was needed to correctly excise the pLD56 plasmid (MluI), (iii) which enzyme cut once only in the pBR322 portion (ClaI) and (iv) which enzyme did not cut in the plasmid at all (ApaI). Southern hybridizations of ClaI and ApaI digests of DNA from ATCC 20774 and DL118 (probed with a BIO-fragment) showed that, as expected, the biotin region of DL118 (when compared to the BIO region of ATCC 20774) was disrupted by an addition of DNA approximately the size of pLD56. MluI digests of DL118 DNA (probed with pBR322) further showed that the addition was the same size as intact pLD56.

Construction of Expression/Secretion Plasmid pLX-34. An expression plasmid has been constructed which places the prorennin coding sequence with XPR2 secretion signals (157 amino acid prepro sequences) downstream of the LEU2 promoter. This expression plasmid demonstrates that a promoter other than the XPR2 promoter can be used to achieve secretion of heterologous proteins. Furthermore, this expression vector is capable of achieving expression/secretion independent of the site of integration in the *Y. lipolytica* genome. Successful secretion of prorennin with a promoter other than the XPR promoter demonstrates the feasibility of an expression vector construction for identifying alternative new strong promoters in *Y. lipolytica*. In addition, this approach can be used to obtain an expression culture with two separate hybrid prorennin genes, one expressed by the LEU2 promoter and the other by the XPR2 promoter, integrated at different sites in the host genome.

Figure 13:
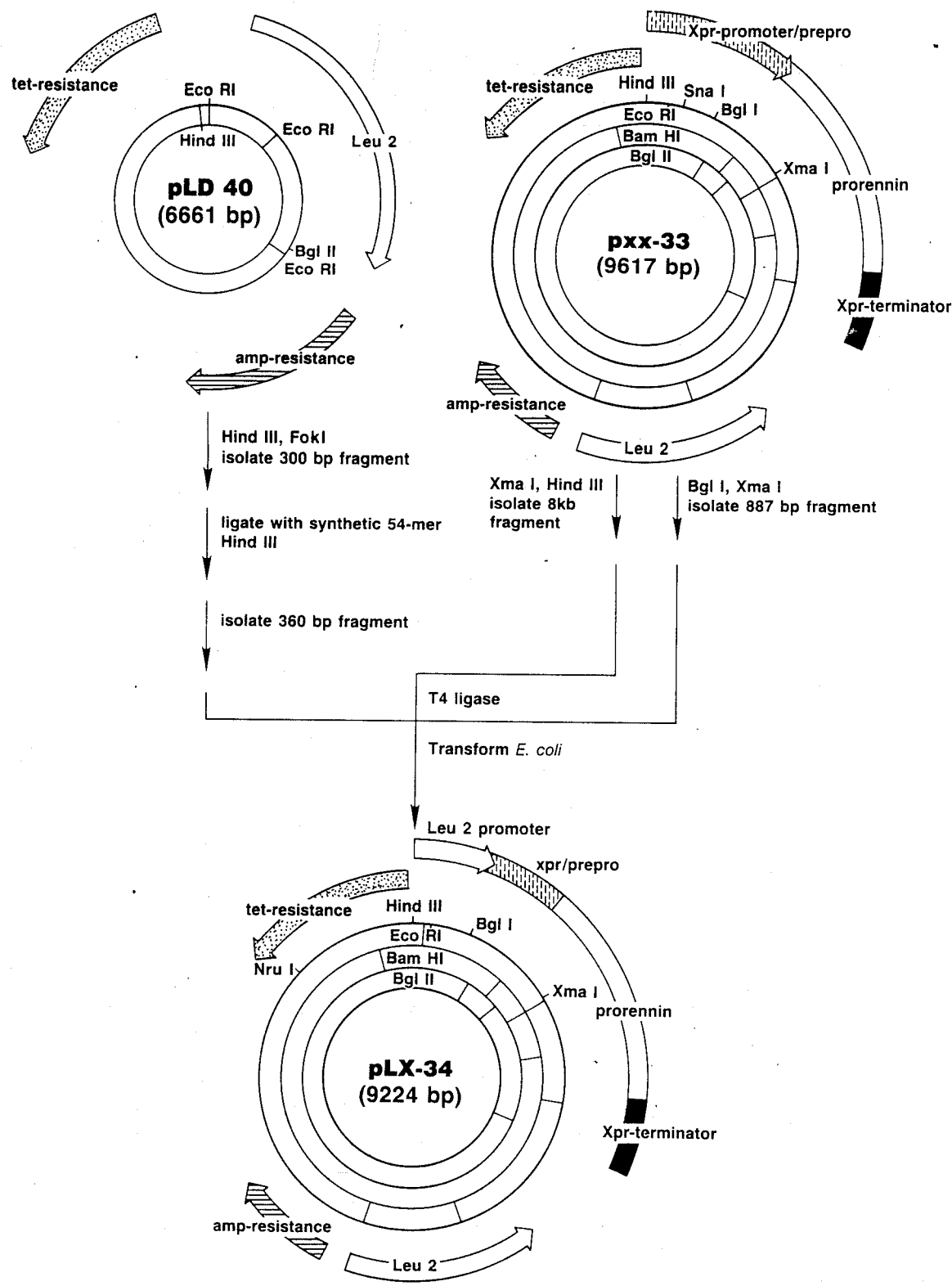
FIG. 13 - Construction sequence and restriction map of plasmid pLX-34.

The experimental steps used for construction of an expression vector which contains the prorennin gene with alkaline protease secretion signals (157 amino acid XPR2 prepro sequence) expressed by LEU2 promoter sequences are outlined in FIG. 13. The construction of this plasmid was initiated by preparing a LEU2 promoter fragment, containing about 300 base pairs of the 5'-untranslated sequence preceding the ATG translational initiation codon of the beta-isopropylmalate dehydrogenase gene (FIG. 12). The 300 bp HindIII-FokI DNA fragment encoding a 270 bp portion of the LEU2 promoter sequence was isolated from the shuttle vector pLD40. This fragment was ligated with a 54 bp synthetic linker with the sequence

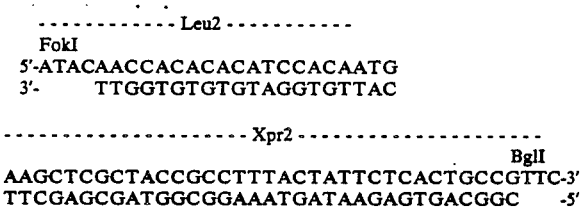

with T4 ligase followed by digestion with HindIII. The resulting ligated sequences were purified by gel electrophoresis isolation of the approximately 360 base pair HindIII-BglII DNA fragment. A second component fragment coding for the remainder of the XPR2 prepro sequence and the first 152 amino acid residues of prorennin was isolated from expression plasmid pXX-33 (FIG. 6) by cleavage with BglII and XmaI, and gel purification of the resulting 887 base pair DNA fragment. A third fragment containing the rest of the prorennin gene, XPR2 terminator, and vector sequences was prepared by cleavage of pXX-33 with HindIII and XmaI, and gel purification by cleavage of the approximately 8.0 kb vector fragment. The three DNA fragments were ligated using the standard procedure described above. The ligation reaction was used to transform *E. coli* K12 strain HB101. Plasmids were isolated from transformants selected on the basis of ampicillin resistance, and plasmid pLX-34 was identified by its restriction map (FIG. 13).

*Y. lipolytica* ATCC 20794 (DL118) was transformed with NruI cleaved pLX-34 DNA to provide *Y. lipolytica* ATCC 20795 (DL251) and the prorennin secreted into the culture fluid by the leucine-independent transformant culture assayed as described above in the case of pLS-3. This transformation procedure directed the integration of pLX-34 into a pBR322 sequence previously introduced into the bio locus in the host chromosome (described above). Integration of pLX-34 at this site was confirmed by Southern analysis.

Using DL118 as a recipient, Southern hybridization experiments were done as follows: NruI digests of DNA from transformants of DL118 (hybridized with a prochymosin probe, for example, when the input plasmid was a prochymosin expression plasmid) precisely excised the input plasmid. A few nanograms of NruI-digested transforming plasmid served to check the correct size of the hybridizing band. Also MluI digests (MluI did not cut in the transforming plasmids) of DNA from these transformants (probed with 32p-labelled pBR322) showed that the resident pBR322 sequence of DL118 was disrupted by addition of one or more molecules of the transforming plasmid. This demonstrated that integration occurred at the desired site.

Transformant culture *Y. lipolytica* ATCC 20795 (DL251) was grown in YEPD media at 22° C. to favor expression by the LEU2 promoter. The presence of prorennin in the culture supernatants was confirmed by the milk clotting assay (see above) of acid activated culture supernatants and verified by immuno-blot analysis (see above). These results show that this hybrid gene is an independent expression unit capable of expression/secretion when integrated at a site other than XPR2 or LEU2. This feature permits construction of an expression culture with multiple hybrid genes potentially capable of achieving enhanced levels of extracellular prorennin.

EXAMPLE 3

Figure 9:
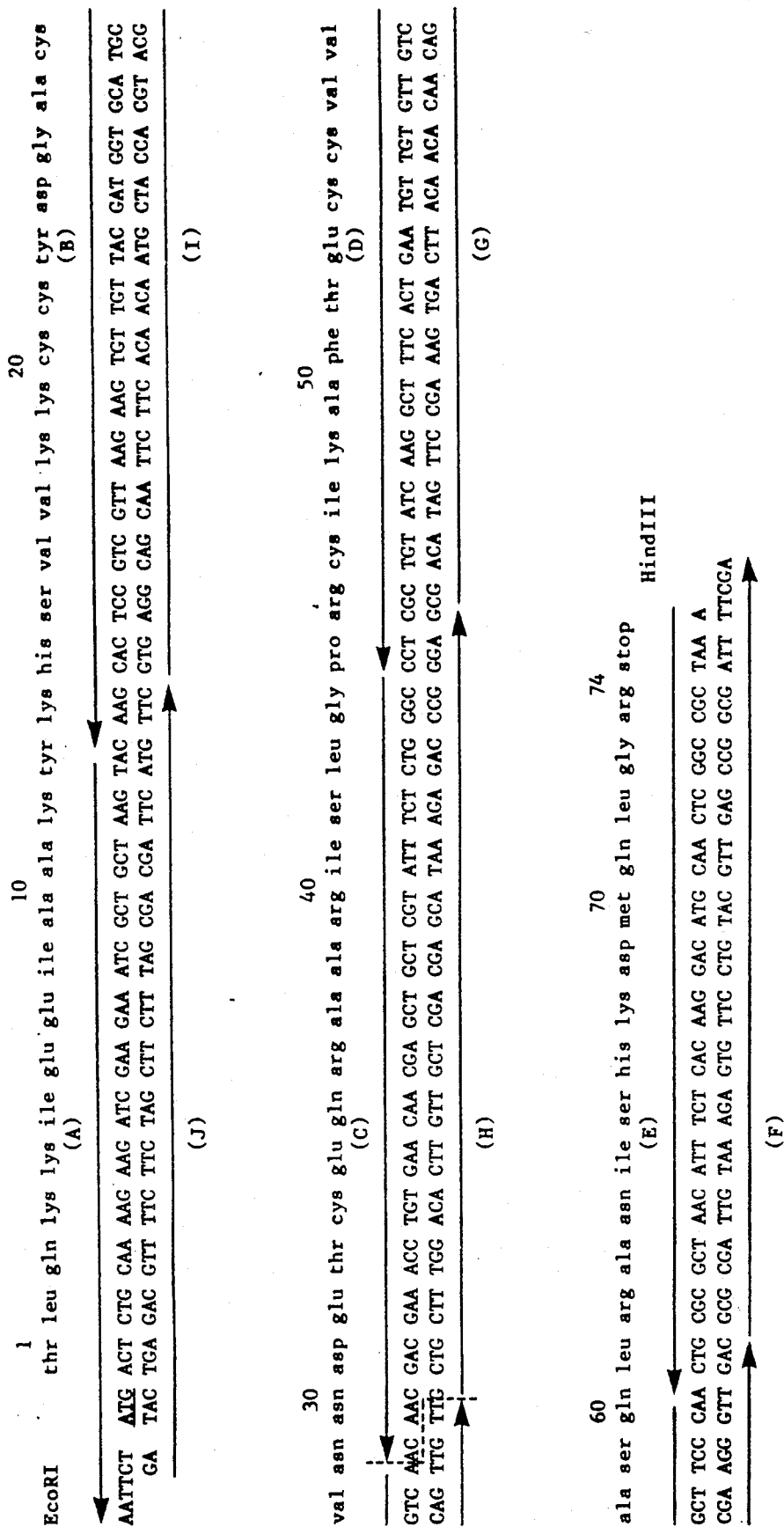

Sequence of Synthetic Gene for Human C5a. The plan devised to achieve bacterial production of human anaphylatoxin C5a was analogous to previous methods used for synthesis and expression of EGF, as described in EP Application No. 0147178. It employed the construction of a gene in which the coding sequence for the activated complement component C5a was made synthetically. Given the known amino acid sequence of human C5a, we designed a DNA fragment encoding the information for its 74 amino acids (FIG. 9). The synthetic gene sequence was chosen to maximize *E. coli* and *S. cerevisiae* preferred codon utilization and allow for several restriction endonuclease sites to facilitate characterization. This approach allowed for direct expression in *E. coli* of anaphylatoxin by introducing an ATG initiation codon for protein synthesis in front of the triplet coding for the first amino acid of the C5a polypeptide. To facilitate its insertion in a desired orientation into plasmid pBR322, the synthetic C5a gene was designed to contain EcoRI and HindIII restriction endonuclease recognition sites at its termini. To produce the resulting C5a gene sequence, ten 47-mers were synthesized by the phosporamidite method and assembled into a 235 bp double stranded DNA fragment. The C5a gene fragment was inserted into appropriately cleaved pBR322 and the cloned gene identified by restriction cleavage analysis of plasmid DNA from arbitrarily chosen transformants. Several C5a clones were then analyzed by DNA sequencing to identify a clone with the correct sequence. The intended nucleotide sequence for the C5a gene region was found in 2 of the 5 clones examined.

Figure 10:
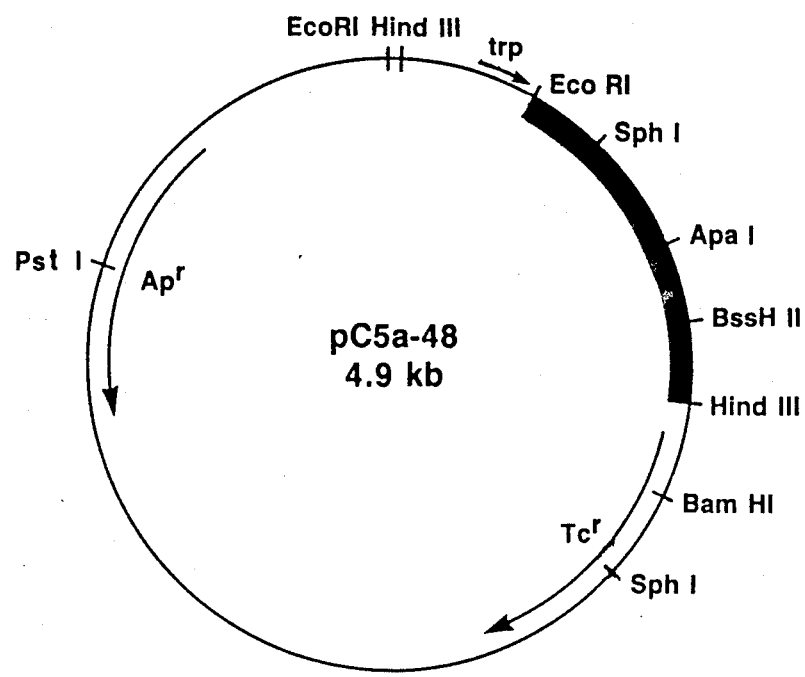
FIG. 10 - Restriction map of plasmid pC5a-48.

Bacterial Expression of Human C5a. The construction of the C5a expression plasmids was initiated by cleavage of the C5a subclone with the restriction endonuclease EcoRI, followed by dephosphorylation by treatment with bacterial alkaline phosphatase. Using a 360 bp EcoRI DNA fragment from pPFZ-R2 containing the trp promoter-operator and ribosome binding site sequences, a C5a expression plasmid was constructed. Competent cells of E. coli strain HB101 were transformed with the ligation reaction. Several drug resistant colonies from each transformation were purified and their plasmid DNAs were subjected to restriction endonuclease mapping analysis to identify those with the trp promoter in orientation which would result in transcription of the C5a gene. Multiple isolates from this ligation reaction were identified with plasmids containing the anaphylatoxin gene adjacent to the bacterial promoter sequence in the configuration required for direct expression of C5a. A restriction map of the C5a expression plasmid pC5a-48 is illustrated in FIG. 10.

Expression and Secretion of Human Anaphylatoxin in *Y. lipolytica.*

Expression/secretion vector pC5aX-3 encoding for the secretion of human anaphylatoxin C5a was prepared using techniques as set forth in Example 1 for pXX-33. *Y. lipolytica* ATCC 20774 was then transformed by this secretion vector and the human C5a produced by the transformed cultures assayed as described above, except goat anti-C5a and rabbit anti-goat IgG were used in the immunoblot procedure. For the plasmid described in this example, the presence of C5a in the culture supernatant was confirmed.

Construction of Expression/Secretion Plasmid pC5aX-3. The experimental steps for construction of the anaphylatoxin expression/secretion plasmid pC5aX-3 are outlined in FIG. 11. This plasmid contains the sequence for the "complete" XPR2 promoter and the 157 amino acid residue signal and pro-peptide joined to a synthetic sequence encoding the 74 amino acid residues of C5a. The construction plan used for pC5aX-3 was similar to that used for pXX-33. First, the plasmid pXHP-24 (or another plasmid containing the desired sequence) was cleaved with. HindIII and AvaI and the 1150 base pair fragment containing the XPR2 promoter was gel purified. A second fragment containing the 3' end of the XPR2 pro-peptide and the C5a structural gene sequence was created by a standard ligation reaction utilizing the approximately 220 base pair HinfI-HindIII DNA fragment from *E. coli* expression plasmid pC5a-48 and the synthetic fragment with the sequence with T4 ligase followed by cleavage with AvaI and HindIII. The resulting ligated sequences were purified by gel electrophoresis selecting the about 250 base pair AvaI-HindIII fragment. The HindIII-AvaI fragment containing the promoter and the AvaI-HindIII fragment encoding C5a were then ligated with T4 ligase followed by digestion with HindIII. The approximately 1.4kb fragment was gel purified and used in a ligation with HindIII cleaved pterm 4 (described above). The ligation reaction was used to transform *E. coli* K12 strain MM294. Plasmids selected for ampicillin resistance were isolated from the selected transformants, and plasmid pC5aX-3 was identified by its restriction map. *Y. lipolytica* strain PC-30869, ATCC 20774, was then transformed with SnaBI cleaved pC5aX-3 and the anaphylatoxin secreted into the culture medium by the transformed cultures assayed as described above. The presence of C5a in the culture supernatant was confirmed by the procedure described above.

It is recognized that many proteins synthesized by ribosomes bound to the endoplasmic reticulum are produced as glycoproteins. In fact, glycosylation may influence the secretion of a given protein. N-linked glycosylation of eukaryotic proteins occurs at the tripeptide sequences asparagine-X-threonine and asparagine-X-serine, where X may be any amino acid except possibly asparate (Hubbard, S., et al. 1981, Ann Rev. Biochem. 50; 555). The amino acid sequence of prorennin includes two such tripeptide sequences, however, gel electrophoretic analysis of the prorennin secreted in *Y. lipolytica* cultures showed no evidence of glycosylation. In other secreted eukaryotic proteins, not all asparagine-X-threonine/serine sites are glycosylated. It is likely that certain asparagines within tripeptide sequences are not glycosylated because they are inaccessible to the glycosylation enzymes.

In the case of human C5a, the amino acid sequence includes a single glycosylation site or tripeptide sequence (Asn-Ile-Ser), which normally possesses a complex oligosaccharide attached to asparagine (Fernandez, H., et al. 1976, J. Immunol. 117, 1688). A portion of the C5a molecules secreted into the *Y. lipolytica* culture medium appear to be glycosylated because a broad region of antigenic activity is seen in the high molecular weight portion of the immunoblot. This heterogeneous electrophoretic mobility is analogous to that observed with other secreted proteins and is probably due to varying degrees of carbohydrate addition. In the present invention, the apparent glycoslyation of certain secreted heterologous proteins suggests that *Y. lipolytica* expression and secretion will be useful for production of many normally glycosylated eukaryotic proteins.

We claim:

1. An isolated DNA sequence which codes for the XPR2 gene of *Y. lipolytica.*

2. An isolated DNA sequence which codes for a polypeptide containing the signal sequence of the alkaline protease precursor encoded by the XPR2 gene of *Y. lipolytica.*

3. An isolated DNA sequence which codes for the promoter region of the XPR2 gene of *Y. lipolytica.*

4. An isolated DNA sequence which codes for the terminator region of the XPR2 gene of *Y. lipolytica.*

```
5'  CCGAGATTCCTGCTTCTTCTAATGCCAAGCGA      3'
3'         CTAAGGACGAAGAAGATTACGGTTCGCTTGA 5'
```

5. An isolated DNA sequence which codes for a polypeptide containing the pro1-, the pro2- or the pro1-pro2-sequence of the alkaline protease precursor encoded by the XPR2 gene of *Y. lipolytica*.

6. An isolated DNA sequence which codes for the sequence which precedes that encoding the N-terminal amino acids of mature alkaline protease and which codes for a polypeptide containing the signal, the pro1- and the pro2-sequences of the alkaline protease precursor encoded by the XPR2 gene of *Y. lipolytica*.

7. An isolated DNA sequence which encodes for: (a) the XPR2 gene of *Yarrowia lipolytica* or a fragment thereof; of (b) at least one of the following: the signal, the pro1- or the pro2-sequence of the XPR2 gene of *Y. lipolytica* and at least one of the following: the LEU2 gene of *Y. lipolytica*, the promoter or the terminator sequence thereof, or the promoter or the terminator sequence of the XPR2 gene of *Y. lipolytica*.

8. A *Y. lipolytica* transformant capable of producing a heterologous protein with a XPR2 signal sequence fused thereto and secreting said heterologous protein, said transformant comprising, integrated into its genome, a coding sequence for said heterologous protein operably linked to a XPR2 signal sequence of *Y. lipolytica* and a promoter which functions in *Y. lipolytica*.

9. A process for producing heterologous protein, or heterologous protein fused to a XPR2 encoded polypeptide, by a *Y. lipolytica* culture which comprises:

(i) introducing into said *Y. lipolytica* an expression vector comprising a DNA sequence encoding a protein heterologous to *Y. lipolytica* and, operably linked thereto, (a) the XPR2 gene of *Y. lipolytica*; or (b) at least one of the following: the signal, the pro1- or the pro2-sequence of the XPR2 gene of *Y. lipolytica* and at least one of the following: the LEU2 gene or the promoter thereof, or the promoter sequence of the XPR2 gene;
(ii) cultivating the thus produced *Y. lipolytica* integrative transformant of (i) in a suitable nutrient medium; and
(iii) recovering the heterologous protein or heterologous protein fused to XPR2 encoded protein.

10. A method of site specific integrative transformation of *Y. lipolytica* which method comprises transforming a *Y. lipolytica* strain, which strain comprises, integrated into its genome, heterologous DNA which comprises a region of homology to a vector, which region serves as a recipient site during integrative transformation, which a nucleotide sequence homologous to said region so as to produce integrative *Y. lipolytica* transformants which comprise heterologous DNA integrated into said recipient site.

11. A method of producing a heterologous protein which comprises cultivating a transformant obtained according to the method of claim 94 wherein said coding sequence is operably linked to a promoter which functions in *Y. lipolytica*.

12. A method of producing a heterologous protein which comprises cultivating a transformant obtained according to the method of claim 95 wherein said coding sequence is operably linked to a promoter which functions in *Y. lipolytica*.

13. A process according to claim 9 wherein the expressive vector comprises a DNA sequence encoding a protein heterologous to *Y. lipolytica* and, operably linked thereto, the XPR2 gene of *Y. lipolytica* and said DNA sequence is inserted between the promoter and terminator sequences of said XPR2 gene.

14. A process for producing heterologous protein by a *Y. lipolytica* transformant according to claim 8 which comprises cultivating said *Y. lipolytica* transformant in a suitable nutrient medium.

15. A method of producing a heterologous protein which comprises the method according to claim 11 and recovering said heterologous protein.

16. A method of producing a heterologous protein which comprises the method according to claim 12 and recovering said heterologous protein.

17. A method of producing a heterologous protein which comprises the method according to claim 14 and recovering said heterologous protein.

18. The nucleotide sequence

19. The nucleotide sequence

20. The nucleotide sequence

21. Recombinant DNA material comprising the nucleotide sequence of claim 7.

22. Recombinant DNA material comprising the nucleotide sequence of claim 1.

23. Recombinant DNA material comprising the nucleotide sequence of claim 2.

24. Recombinant DNA material comprising the nucleotide sequence of claim 3.

25. Recombinant DNA material comprising the nucleotide sequence of claim 6.

26. Recombinant DNA material comprising the nucleotide sequence of claim 8.

27. Recombinant DNA material comprising the nucleotide sequence of claim 9.

28. Recombinant DNA material comprising the nucleotide sequence of claim 12.

29. Recombinant DNA material according to claim 21 wherein said material is a *Y. lipolytica* expression vector.

30. Recombinant DNA material according to claim 22 wherein said material is a *Y. lipolytica* expression vector.

31. Recombinant DNA material according to claim 24 wherein said material is a *Y. lipolytica* expression vector.

32. Recombinant DNA material according to claim 26 wherein said material is a *Y. lipolytica* expression vector.

33. Recombinant DNA material according to claim 27 wherein said material is a *Y. lipolytica* expression vector.

34. Recombinant DNA material according to claim 28 wherein said material is a *Y. lipolytica* expression vector.

35. Recombinant DNA material according to claim 21 wherein said material is chromosomal DNA of a *Yarrowia lipolytica* integrative transformant.

36. Recombinant DNA material according to claim 22 wherein said material is chromosomal DNA of a *Yarrowia lipolytica* integrative transformant.

37. Recombinant DNA material according to claim 24 wherein said material is chromosomal DNA of a *Yarrowia lipolytica* integrative transformant.

38. A vector comprising a XPR2 signal sequence encoding region and a promoter sequence of a *Y. lipolytica* XPR2 or LE12 gene fused to a gene for a heterologous protein.

39. A vector according to claim 38 wherein said promoter sequence is that of the XPR2 gene of *Y. lipolytica*.

40. A vector according to claim 38 wherein said promoter sequence is that of the LEU2 gene of *Y. lipolytica*.

41. A vector comprising a nucleotide sequence according to claim 7.

42. A vector comprising a nucleotide sequence according to claim 1.

43. A vector comprising a nucleotide sequence according to claim 3.

44. A vector comprising a nucleotide sequence according to claim 5.

45. A vector comprising a nucleotide sequence according to claim 6.

46. A vector comprising a nucleotide sequence according to claim 18.

47. A vector comprising a nucleotide sequence according to claim 19.

48. A vector comprising a nucleotide sequence according to claim 20.

49. A vector comprising the nucleotide sequence of a gene heterologous to said *Y. lipolytica*, and a nucleotide sequence according to claim 7.

50. A vector according to claim 49 wherein said heterologous gene sequence is operably linked to said nucleotide sequence.

51. A vector according to claim 50 wherein said heterologous gene is the prorennin gene or the human anaphylatoxin C5a gene.

52. *Y. lipolytica* transformant according to claim 8 wherein said promoter DNA sequence is derived from a *Y. lipolytica* gene.

53. *Y. lipolytica* transformed with a vector according to claim 41.

54. *Y. lipolytica* transformed with a vector according to claim 42.

55. *Y. lipolytica* transformed with a vector according to claim 43.

56. *Y. lipolytica* transformed with a vector according to claim 44.

57. *Y. lipolytica* transformed with a vector according to claim 45.

58. *Y. lipolytica* transformed with a vector according to claim 46.

59. *Y. lipolytica* transformed with a vector according to claim 47.

60. *Y. lipolytica* transformed with a vector according to claim 48.

61. *Y. lipolytica* transformed with a vector according to claim 49.

62. *Y. lipolytica* transformed with a vector according to claim 50.

63. *Y. lipolytica* transformed with a vector according to claim 51.

64. Plasmid pLs-3.

65. Plasmid pXX-33.

66. Plasmid pXX-22.

67. Plasmid pXX-11.

68. Plasmid pXHP-24.

69. Plasmid pC5aX-3.

70. Plasmid pLD56.

71. Plasmid pLX-34.

72. *Y. lipolytica* transformant comprising the transformant of *Y. lipolytica* ATCC 20774 with plasmid pXX-33, the vector according to claim 65, said transformant having the identifying characteristics of ATCC 20780.

73. *Y. lipolytica* ATCC 20780.

74. *Y. lipolytica* transformant comprising the transformant of *Y. lipolytica* ATCC 20774 with plasmid pXX-22, the vector according to claim 66, said transformant having the identifying characteristics of ATCC 20779.

75. *Y. lipolytica* ATCC 20779.

76. *Y. lipolytica* transformant comprising the transformant of *Y. lipolytica* ATCC 20774 with plasmid pXX-11, the vector according to claim 67, said transformant having the identifying characteristics of ATCC 20778.

77. *Y. lipolytica* ATCC 20778.

78. *Y. lipolytica* transformant comprising the transformant of *Y. lipolytica* ATCC 20774 with XPR2 gene of *Y. lipolytica*, said transformant having the identifying characteristics of ATCC 20781.

79. *Y. lipolytica* ATCC 20781.

80. *Y. lipolytica* transformant comprising the transformant of *Y. lipolytica* ATCC 20774 with plasmid pC5aX-3, the vector according to claim 69, said transformant having the identifying characteristics of ATCC 20777.

81. *Y. lipolytica* comprising the transformant of *Y. lipolytica* ATCC 20688 with circular plasmid pLS-3, the vector according to claim 64, said transformant having the identifying characteristics of ATCC 20775.

82. *Y. lipolytica* ATCC 20775.

83. *Y. lipolytica* comprising the transformant of *Y. lipolytica* ATCC 20688 with SnaB1 digested plasmid pLS-3, said transformant having the identifying characteristics of ATCC 20776.

84. *Y. lipolytica* ATCC 20776.

85. *Y. lipolytica* having the identifying characteristics of ATCC 20774.

86. *Y. lipolytica* ATCC 20774.

87. A process according to claim 9 wherein said heterologous protein DNA sequence is the prorennin or human anaphylatoxin C5a sequence.

88. A process for producing prorennin which comprises cultivating a *Y. lipolytica* transformant according to claim 72 in a suitable nutrient medium.

89. A process for producing prorennin which comprises cultivating a *Y. lipolytica* transformant according to claim 74 in a suitable nutrient medium.

90. A process for producing prorennin which comprises cultivating a *Y. lipolytica* transformant according to claim 76 in a suitable nutrient medium.

91. A process for producing human anaphylatoxin C5a which comprises cultivating a *Y. lipolytica* transformant according to claim 80 in a suitable nutrient medium.

92. A process for producing a heterologous protein which comprises cultivating the transformant of *Y. lipolytica* ATCC 20777 in a suitable nutrient medium.

93. The method according to claim 10 wherein said region of homology is derived from pBR322 or a derivative thereof.

94. The method according to claim 10 wherein the nucleotide sequence used for transformation further comprises a coding sequence for a heterologous protein.

95. The method according to claim wherein the nucleotide sequence used for transformation further comprises a coding sequence for a heterologous protein.

96. A *Y. lipolytica* integrative transformant which does not produce alkaline protease, said transformant comprising an XPR+ strain transformed with an XPR expression vector which vector comprises a fragment of the XPR2 gene missing regulatory or structural components at both ends of the gene.

97. A process for detecting *Y. lipolytica* transformants having vector DNA integrated at the XPR2 gene which comprises:
(i) transforming an XPR+ strain of *Y. lipolytica* with an XPR expression construct which construct comprises a fragment of the XPR2 gene missing regulatory or structural components at both ends of the gene; and
(ii) screening the transformants produced in (i) for loss of alkaline protease activity.

98. A process according to claim 97 wherein said XPR+ *Y. lipolytica* strain is transformed with circular plasmid pLS-3 DNA or with SnaBI digested pLS-3 DNA.

99. A process according to claim 97 wherein said *Y. lipolytica* is *Y. lipolytica* ATCC 20688.

100. *Y. lipolytica* transformant comprising the transformant of *Y. lipolytica* ATCC 20794 with NruI cleaved pLX-34, the vector according to claim 71, said transformant having the identifying characteristics of ATCC 20795.

101. *Y. lipolytica* ATCC 20795.

102. *Y. lipolytica* transformant comprising the transformant of *Y. lipolytica* ATCC 20774 with pLD56, the plasmid according to claim 70, said transformant having the identifying characteristics of ATCC 20794.

103. *Y. lipolytica* ATCC 20794.

104. Process for producing prorennin which comprises cultivating a *Y. lipolytica* transformant according to claim 100 in a suitable nutrient medium.

* * * * *

UNITED STATES PATENT AND TRADEMARK OFFICE
CERTIFICATE OF CORRECTION

PATENT NO. : 4,937,189

DATED : June 26, 1990

INVENTOR(S) : Lance S. Davidow et al.

It is certified that error appears in the above-identified patent and that said Letters Patent is hereby corrected as shown below:

Column 9, line 14, insert --ATCC 68127 transformant of E. coli K-12 with pXHP-24--;

Column 11, line 55, "ATCC 206287" should read --ATCC 20628--;

Column 12, line 15, "D-giotin" should read --D-biotin--;

Column 14, line 45, before "strain" insert --The host--;

Column 17, line 11, "pL,S-3" should read --pLS-3--;

Column 20, line 35, "gate" should read --gene--;

Claim 7, column 27, line 13, "of" (first occurence) should read- --or--.

Claim 26, column 28, line 49, "8" should read --18--;

Claim 27, column 28, line 51, "9" should read --19--;

Claim 28, column 28, line 53, "12" should read --20--; and

Claim 95, column 31, line 7, after "claim" insert --93--.

Signed and Sealed this

Fourth Day of February, 1992

Attest:

HARRY F. MANBECK, JR.

*Attesting Officer*　　　　*Commissioner of Patents and Trademarks*

UNITED STATES PATENT AND TRADEMARK OFFICE
CERTIFICATE OF CORRECTION

PATENT NO. : 4,937,189

DATED : June 26, 1990

INVENTOR(S) : Lance S. Davidow et al.

It is certified that error appears in the above-identified patent and that said Letters Patent is hereby corrected as shown below:

<u>In the Drawings:</u>

Figure 8, below "pxhp24", "HindIII,BglII" should read -- HindIII,BglI --; and

Column 20, line 67, "HindIII-BglII" should read -- HindIII-BglI --.

Signed and Sealed this

Twenty-second Day of September, 1992

Attest:

DOUGLAS B. COMER

Attesting Officer     Acting Commissioner of Patents and Trademarks